US009096519B2

(12) United States Patent
Morandi et al.

(10) Patent No.: US 9,096,519 B2
(45) Date of Patent: Aug. 4, 2015

(54) PROCESS FOR THE SYNTHESIS OF KETONES FROM INTERNAL ALKENES

(71) Applicant: California Institute of Technology, Pasadena, CA (US)

(72) Inventors: Bill Morandi, Pasadena, CA (US); Robert H. Grubbs, South Pasadena, CA (US); Zachary K. Wickens, Pasadena, CA (US); Michael M. Lerch, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/149,924

(22) Filed: Jan. 8, 2014

(65) Prior Publication Data

US 2014/0194604 A1 Jul. 10, 2014

Related U.S. Application Data

(60) Provisional application No. 61/750,958, filed on Jan. 10, 2013.

(51) Int. Cl.
| | |
|---|---|
| *C07C 303/30* | (2006.01) |
| *C07C 303/40* | (2006.01) |
| *C07D 209/48* | (2006.01) |
| *C07C 45/28* | (2006.01) |
| *C07C 67/29* | (2006.01) |
| *C07C 201/12* | (2006.01) |
| *C07C 231/12* | (2006.01) |
| *C07C 247/04* | (2006.01) |
| *C07C 67/313* | (2006.01) |
| *C07C 51/373* | (2006.01) |
| *C07B 41/06* | (2006.01) |

(52) U.S. Cl.
CPC .............. *C07D 209/48* (2013.01); *C07B 41/06* (2013.01); *C07C 45/28* (2013.01); *C07C 51/373* (2013.01); *C07C 67/29* (2013.01); *C07C 67/313* (2013.01); *C07C 201/12* (2013.01); *C07C 231/12* (2013.01); *C07C 247/04* (2013.01); *C07C 303/30* (2013.01); *C07C 303/40* (2013.01); *C07C 2101/14* (2013.01)

(58) Field of Classification Search
CPC ............................ C07C 303/30; C07C 303/40
USPC ........................................................ 534/555
See application file for complete search history.

(56) References Cited

U.S. PATENT DOCUMENTS

| | | | |
|---|---|---|---|
| 4,661,642 | A | 4/1987 | Feringa |
| 5,506,363 | A | 4/1996 | Grate et al. |
| 2012/0172634 | A1 | 7/2012 | Dong et al. |
| 2014/0316149 | A1 | 10/2014 | Wickens et al. |

FOREIGN PATENT DOCUMENTS

EP 0395792 9/1995

OTHER PUBLICATIONS

Dong et al, "Palladium-Catalyzed Selective Anti-Markovnikov Oxidation of Allylic Esters", Angew. Chem. Int. Ed., 2013, 52, 5561-5565.
Dong et al, "Palladium-Catalyzed Selective Anti-Markovnikov Oxidation of Allylic Esters", Angw. Chem., May 2013, 125(21), 5671-5675.
Miller, D.G. and Wayner, D.D., "Improved Method for the Wacker Oxidation of Cyclic and Internal Olefins", J. Org. Chem., 1990, 55(9), 2924-2927.
Mitsudome et al, "Highly Atom-Efficient Oxidation of Electron-Deficient Internal Olefins to Ketones Using a Palladium Catalyst", Angew. Chem. Int. Ed., Apr. 22, 2013, 52, 5961-5964.
Mitsudome et al, "Simple and Clean Synthesis of Ketones From Internal Olefins Using PdCl2/N,N-dimethylacetamide Catalyst System", Tetrahedron Letters, 54, Jan. 17, 2013, 1596-1598.
Mitsudome et al, "Wacker-Type Oxidation of Internal Olefins Using a PdC12/N,Ndimethylacetamide Catalyst System under Copper-Free Reaction Conditions", Angew. Chem. Int. Ed., 2010, 49, 1238-1240, published online: Dec. 28, 2009.
Morandi et al, "RegioselectiveWacker Oxidation of Internal Alkenes: Rapid Access to Functionalized Ketones Facilitated by Cross-Metathesis", Angew. Chem. Int. Ed., Jul. 26, 2013, 52, 9751-9754.
Piera, J. and Backvall, J.E., "Catalytic Oxidation of Organic Substrates by Molecular Oxygen and Hydrogen Peroxide by Multistep Electron Transfer—A Biomimetic Approach", Angew. Chem. Int. Ed. 2008, 47, 3506-3523.
Anderson et al., "Experimental and Computational Study of a Direct $O_2$-Coupled Wacker Oxidation: Water Dependence in the Absence of Cu Salts", J. Am. Chem. Soc., 2010, 132(34), 11872-11874.
Bäckvall et al., "Stereo- and Regioselective Palladium-Catalyzed 1,4-Diacetoxylation of 1,3-Dienes", J. Org. Chem., 1984, 49, 4619-4631.
Bäckvall et al., "Biomimetic Adrobic 1,4-Oxidation of 1,3-Dienes Catalyzed by Cobalt Tetraphenylporphyrin-Hydroquinone-Palladium(II). An Example of Triple Catalysis", J. Am. Chem. Soc., 1987, 109(15), 4750-4752.

(Continued)

*Primary Examiner* — Shawquia Jackson
(74) *Attorney, Agent, or Firm* — Baker & Hostetler LLP

(57) ABSTRACT

The present invention is directed to methods for oxidizing internal olefins to ketones. In various embodiments, each method comprising contacting an organic substrate, having an initial internal olefin, with a mixture of (a) a biscationic palladium salt; and (b) an oxidizing agent; dissolved or dispersed in a solvent system to form a reaction mixture, said solvent system comprising at least one $C_{2-6}$ carbon nitrile and optionally at least one secondary alkyl amide, said method conducted under conditions sufficient to convert at least 50 mol % of the initial internal olefin to a ketone, said ketone positioned on a carbon of the initial internal olefin. The transformation occurs at room temperature and shows wide substrate scope. Applications to the oxidation of seed oil derivatives and a bioactive natural product are described.

34 Claims, 2 Drawing Sheets

(56) References Cited

OTHER PUBLICATIONS

Bäckvall et al., "Multi-Step Catalysis for the Oxidation of Oleftns to Ketones by Molecular Oxygen in Chloride Free Media", Tetrahedron Letters, 1988, 29(23), 2885-2888.
Bäckvall et al., "Multistep Electron Transfer in Palladium-Catalyzed Aerobic Oxidations via a Metal Macrocycle-Quinone System", J. Am. Chem. Soc., 1990, 112, 5160-5166.
Beller, "A Personal View on Homogeneous Catalysis and its Perspectives for the Use of Renewables", Eur. J. Lipid Sci. Technol., 2008, 110(9), 789-796.
Campbell et al., "Overcoming the 'Oxidant Problem': Strategies to Use O2 as the Oxidant in Organometallic C—H Oxidation Reactions Catalyzed by Pd (and Cu)", Acc. Chem. Res., 2012, 45(6), 851-863.
Caterina et al., "The Capsaicin Receptor: A Heat-Activated Ion Channel in the Pain Pathway", Nature, 1997, 389, 816-824.
Chen et al., "Discovery and Characterization of a Potent and Selective Antagonist of Melanin-Concentrating Hormone Receptor 2", Biorg. Med. Chem Lett., 2012, 22, 363-366.
Chen et al, "Serial Ligand Catalysis: A Highly Selective Allylic C—H Oxidation", J. Am. Chem. Soc., 2005, 127, 6970-6971.
Corma et al., "Chemical Routes for the Transformation of Biomass into Chemicals", Chem. Rev., 2007, 107(6), 2411-2502.
Cornell et al., "Discovery of a Practical Direct $O_2$-Coupled Wacker Oxidation with Pd[(−)-sparteine]$Cl_2$", Org. Lett., 2006, 8(18), 4117-4120.
Cornell et al., "Recent Progress in Wacker Oxidations: Moving Toward Molecular Oxygen as the Sole Oxidant", Inorg. Chem., 2007, 46(6), 1903-1909.
Decharin et al., "Benzoquinone-Promoted Reaction of $O_2$ with a $Pd^{II}$-Hydridge", J. Am. Chem. Soc., 2011, 133(15), 5732-5735.
Dong et al., "Primary Alcohols from Terminal Olefines: Formal Anit-Markovnikov Hydration via Triple Relay Catalysis", Science, 2011, 333, 1609-1612.
Dounay et al., "Total Synthesis of the Styrchnos Alkaloid (+)-Minfiensine: Tandem Enantioselective Intramolecular Heck-Iminium Ion Cyclization", J. Am. Chem. Soc., 2008, 130(15), 5368-5377.
Fujiwara et al., "Direct C—H Functionalization of Quinones with Boronic Acids", J. Am. Chem. Soc., 2011, 133(10), 3292-3295.
Gligorich et al., "Recent Advancements and Challenges of Palladium$^{II}$-catalyzed Oxidation Reactions with Molecular Oxygen as the Sole Oxidant", Chem. Commun., 2009, 26, 3854-3867.
Grennberg et al., "Acid-Induced Transferomation of Palladium(0)-Benzoquinone Complexes to Palladium(II) and Hydroquinone", Organometallics, 1993, 12(5), 1790-1793.
Grubbs, Handbook of Metathesis, Wiley-VCH 2003, vol. 1, 16 pages.
Harrak et al., "Galacto-Configured Aminocyclitol Phytoceramides are Potent in Vivo Invariant Natural Killer T Cell Stimulators", J. Am. Chem. Soc., 2011, 133(31), 12079-12084.
Hoover et al., "A Highly Practical Cooper(I)/TEMPO Catalyst System for Chemoselective Aerobic Oxidation of Primary Alcohols", J. Am. Chem. Soc. 2011, 133, 16901-16910.
Hudson et al., "Nosteroidal 2,3-Dihydroquinoline Glucocorticoid Receptor Agonists with Reduced PEPCK Activation", Bioorg. Med. Chem. Lett., 2011, 21(6), 1654-1657.
Hull et al., "Mechanism of Benzoquinone-Promoted Palladium-Catalyzed Oxidative Cross-Coupling Reactions", J. Am. Chem. Soc., 131(28), 2009, 9651-9653.
Ito et al., "Induction of Apoptosis in Leukemic Cells by Homovanillic Acid Derivative, Capsaicin, Through Oxidative Stress", Cancer Research, 2004, 64, 1071.
Kissin, "Vanilloid-Induced Conduction Analgesia: Selective, Dose-Dependent, Long-Lasting, with a Low Level of Potential Neurotoxicity", Anesth. Analg., 2008, 107(1), 271-281.
Kwong et al., "A General,Efficient, and Inexpensive Catalyst System for the Coupling of Aryl Iodides and Thiols", Org. Lett., 2002, 4(20), 3517-3520.
Lee et al., "A Facile and Efficient Synthesis of 4-hydroxy-2,6-cis-tetrahydropyrans via Tandem Cross-Metathesis/Thermal S(N)2' Reaction: Protecting-Group-Free Synthesis of (+/−)-diospongin A.", Org. Lett., 2009, 11(22), 5202-5205.
Liu et al., "Highly Regioselective Pd-Catalyzed Intermolecular Aminoacetoxylation of Alkenes and Evidence for cis-Aminopalladation and $S_N2$ C—O Bond Formation", J. Am. Chem. Soc., 2006, 128(22), 7179-7181.
Martinez et al., "Palladium-Catalyzed Vicinal Difunctionalization of Internal Alkenes: Diastereoselective Synethesis of Diamines", Angew. Chem. Int. Ed., 2012, 51(28), 7031-7034.
Michel et al., "A General and Efficien Catalysts System for a Wacker-Type Oxidation Using TBHP as the Terminal Oxidant: Application to Classically Challenging Substrates", J. Am. Chem. Soc., 2009, 131, 6076-6077.
Miller et al., "Electrode-Mediated Wacker Oxidation of Cyclic and Internal Olefins", Can. J. Chem., 1992, 70(9), 2485-2490.
Mitsudome et al., "Convenient and Efficient Pd-Catalyzed Regioselective Oxyfunctionalization of Terminal Olefins by Using Molecular Oxygen as Sole Reoxidant", Angew. Chem. Int. Ed., 2006, 45(3), 481-485.
Mitsudome et al., "Convenient and Efficient Pd-Catalyzed Regioselective Oxyfunctionalization of Terminal Olefins by Using Molecular Oxygen as Sole Reoxidant", Angew. Chem. 2006, 118, 495-499.
Mori et al., "Capsaicin, a Component of Red Peppers, Inhibits the Growth of Androgen-Independent, p53 Mutant Prostate Cancer Cells", Cancer Res., 2006, 66, 3222-3229.
Mukherjee et al., "A Diversity-Oriented Synthesis of Bicyclice cis-Dihydroarenediols, cis-4-Hydroxyscytalones, and Bicyclic Conduritol Analogues", Org. Lett., 2010, 12(11), 2472-2475.
Narute et al., "A [Pd]-Mediated w-alkynone ycloisomerization Approach for the Central Tetrahydropyran Unit and the Synthesis of C(31)-C(48) Fragment of Aflastatin A", Org. Biomol. Chem., 2011, 9, 5469-5475.
Raffier et al., "Desymmetrization of Hepta-1,6-dien-4-ol by Prins Reaction and Subsequent Cross-Metathesis: Access to Diospongine A Homologues", Synthesis, 2011, 24, 4037-4044.
Sato et al., "Asymmetric Cyclization of w-Formyl-1,3-Dienes Catalyzed by a Zerovalent Nickel Complex in the Presence of Silanes", J. Org. Chem., 2002, 67(26), 9310-9317.
Stahl, S., Cover Picture, Angewandte Chem., 2004, 116, 3480.
Stahl, "Palladium Oxidase Catalysis: Selective Oxidation of Organic Chemicals by Direct Dioxygen-Coupled Turnover", Angew. Chem. Intl. Ed., 2004, 43(26), 3400-3420.
Sun et al., "Nonpeptidic and Potent Small-Molecule Inhibitors of cIAP-1/2 and XIAP Proteins", J. Med. Chem, 2010, 53(17), 6361-6367.
Teo et al., "Efficient and Highly Aldehyde Selective Wacker Oxidation", Org. Lett., 2012, 14(13), 3237-3239.
Trost et al., "Synthetic Strageies to Acetogenins. They hydroxybutenolide Terminus", Tetrahedron Lett., 1995, 36(34), 6021-6024.
Tseng et al., "A Modular Synthesis of Salvileucalin B. Structural Domaines", Org. Lett., 2011, 13(16), 4410-4413.
Tsuji et al., "Synthetic Applications of the Palladium-Catalyzed Oxidation of Olefins to Ketones", Synthesis, 1984, 369-384.
Wang et al., "Supercritical Carbon Dioxide and Poly(Ethylene Glycol): An Environmentally Benign Biphasic Solvent System for Aerobic Oxidation of Styrene", Green Chem., 2007, 9, 882-887.
Wang et al., "Palladium-Catalyzed Direct Oxidation of Alkenes with Molecular Oxygen: General and Practical Methods for the Preparation of 1,2-Diols, Aldehydes, and Ketones", J. Org. Chem., 2010, 75(7), 2321-2326.
Weiner et al., "Aldehyde Selective Wacker Oxidations of Phthalimide Protected Allylic Amines: A New Catalytic Route to $\beta^3$-Amino Acids", J. Am. Chem. Soc., 2009, 131, 9473-9474.
Zhou et al., "A General and Convenient Catalytic Synthesis of Nitriles from Amides and Silanes", Org. Lett. 2009, 11(11), 2461-2464.
Andrews et al., "The Transition-Metal Nitro-Nitrosyl Redox Couple: Catalytic Oxidation of Olefins to Ketones", J. Am. Chem. Soc., 1981, 103(10), 2894-2896.

(56) References Cited

OTHER PUBLICATIONS

Beller et al., "Catalytic Markovnikov and Anti-Markovnikov Functionalization of Alkenes and Alkynes: Recent Developments and Trends", Angew. Chem. Int. Ed., 2004, 43(26), 3368-3398, Published Online: Jun. 22, 2004.

Bronner et al., "Formal Anti-Markovnikov Hydroamination of Terminal Olefins", Chemical Science, 2013, 5, 101-106, Published Online: Sep. 19, 2013.

Chowdhury et al., "An Iron Catalyzed Regioselective Oxidation of Terminal Alkenes to Aldehydes", Chem. Commun., 2012, 48, 5497-5499, Published Online: Apr. 17, 2012.

Clyne et al., "The Synthesis of 14-Membered Macrocyclic Ethers", Tetrahedron, Nov. 26, 1999, 55(48), 13659-13682.

Conley et al., "Discovery, Applications, And Catalytic Mechanisms of Shvo's Catalyst", Chem. Rev., Jan. 2010, 110(4), 2294-2312.

Eilbracht et al., "Tandem Reaction Sequences Under Hydroformylation Conditions: New Synthetic Applications of Transition Metal Catalysis", Chem. Rev., Oct. 1999, 99(11), 3329-3365.

Feringa, "Catalytic Oxidation of Alk-1-enes to Aldehydes", J. Chem. Soc., 1986, 909-910.

Fischetti et al., "The Mechanism of Reactions of Organopalladium Salts with Vinylcyclopropanes", J. Organomet. Chem., Sep. 1, 1985, 293(3), 391-405.

Friestad et al., "Aldehyde-Selective Wacker Oxidation in a Thiyi-Mediated Vinyl Group Transfer Route to Daunosamine", Org. Lett., 2007, 9(5), 777-780.

Ghosh et al., "Cu(II)-Catalyzed Olefin Migration and Prins Cyclization: Highly Diastereoselective Synthesis of Substitute Tetrahydropyrans", Org. Lett., 2011, 13(16),4328-4331, Publication Online: Jul. 28, 2011.

Gooch, "Moving Past Markovnikov's Rule", J. Chem. Educ., 2001, 78(10), 1358, Publication Online: Oct. 1, 2001.

Gorczynski et al., "Activation of Peroxisome Proliferator-Activated Receptor y (PPARy) by Nitroalkene Fatty Acids: Importance of Nitration Position and Degree of Unsaturation", J. Med. Chem., 2009, 52(15), 4631-4639, Publication Online: Jul. 17, 2009.

Haggin, "Chemists Seek Greater Recognition for Catalysis", Chem. Eng. News, 1993,71, 23-27.

Hintermann, "Recent Developments in Metal-Catalyzed Additions of Oxygen Nucleophiles to Alkenes and Alkynes", Topics in Organomet. Chem., May 2010, 31, 123-155.

Hosokawa et al., "Palladium(II)_catalyzed Oxidation of Carbon-Carbon double bonds of Allylic Compounds with Molecular Oxygen; Regioselective Formation of Aldehydes", J. Chem. Soc., Chem. Commun., 1991, 21, 1559-1560.

Jira, "Acetaldehyde from Ethylene-A Retrospective on the Discovery of the Wacker Process", Angew. Chem. Int. Ed., Oct. 2009, 48(48), 9034-9037.

Kharasch et al., "Addition of Carbon Tetrachloride and Chloroform to Olefins", Science, Aug. 3, 1945, 102(2640), 128.

Lai et al., "Reversal of Regiochemistry of Wacker-Type Reactions Oriented by Heteroatoms", J. Org. Chem., Jun. 1992, 57(12), 3485-3487.

Lopez et al., "Regia- and Enantioselective Iridium-Catalyzed Intermolecular Allylic Etherification of Achiral Allylic Carbonates with Phenoxides", J. Am. Chem. Soc., 2003, 125(12),3426-3427, Publication Online: Mar. 4, 2003.

Mahatthananchai et al., "Catalytic Selective Synthesis", Angew. Chem. Int. Ed., Oct. 29, 2012, 51, 10954-10990.

Maity et al., "Efficient and Stereoselective Nitration of Mono- and Disubstituted Olefins with AgN02 and TEMPO", J. Am. Chem. Soc., 2013, 135(9), 3355-3358.

Michel et al., "Catalyst-Controlled Wacker-Type Oxidation of Protected Allylic Amines", Angew. Chem. Int. Ed., Sep. 24, 2010, 49, 7312-7315.

Müller et al., "Hydroamination: Direct Addition of Amines to Alkenes and Alkynes", Chem. Rev., 2008, 108(9), 3795-3892, Publication Online: Aug. 26, 2008.

Muzart, "Aldehydes from Pd-Catalysed Oxidation of Terminal Olefins", Tetrahedron, Aug. 6, 2007, 63(32), 7505-7521.

Nagano et al., "Combined Lewis Acid Catalysts in Shotgun Process: A Convenient Synthesis of the Female Sex Pheromone of the Red-Bollworm Moth", Tetrahedron, Oct. 7, 2002, 58(41), 8211-8217.

Raghavan et al., "An Efficient Stereoselective Synthesis of Penaresidin a from (E)-2-Protected Amino-3,4-unsatured Sulfoxide", J. Org. Chem., 2010, 75, 748-761, Publication Online: Dec. 21, 2009.

Ritter et al., "A Standard System of Characterization for Olefin Metathesis Catalysts", Organometallics, 2006, 25(24), 5740-5745, Publication Online: Oct. 20, 2006.

Seayad et al., "Internal Olefins to Linear Amines", Science, Sep. 6, 2002, 297(5587), 1676-1678.

Sigman et al., "Imparting Catalyst Control Upon Classical Palladium-Catalyzed Alkenyl C-H Bond Functionalization Reactions", Acc. Chem. Res., 2012, 45(6), 874-884.

Smidt et al., "Katalytische Umsetzungen von Olefinen an Platinmetaii-Verbindungen", Angew. Chem. Int., 1959, 71(5), 176-182, with English Abstract.

Stowers et al., "Nitrate as a Redox Co-Catalyst for the Aerobic Pd-Catalyzed Oxidation of Unactivated $sp^3$ -C-H Bonds", Chem. Sci., 2012, 3, 3192-3195.

Wang et al., "A Versatile Catalyst for Reductive Amination by Transfer Hydrogenation", Angew. Chem. Int. Ed., 2010, 49, 7548-7552.

Wang et al., "Pd(II)-Catalyzed Hydroxyl-Directed C-H Activation/C-O Cyclization: Expedient Construction of Dihydrobenzofurans", J. Am. Chem. Soc., 2010, 132(35), 12203-12205, Publication Online: Jan. 10, 2013.

Wenzel, "Oxidation of Olefins to Aldehydes Using a Palladium-Copper Catalyst", J. Chem. Soc., 1993, 862-864.

Wenzel, "Cationic Palladium Nitro Complexes as Catalysts for the Oxygen-based Oxidation of Alkenes to Ketones, and for the Oxydehydrogenation of Ketones and Aldehydes to the Unsaturated Analogues", J. Chem. Soc., Chem. Commun., 1989, 932-933.

Wickens et al., "Aldehyde-Selective Wacker-Type Oxidation of Unbiased Alkenes Enabled by a Nitrite Co-Catalyst", Angew. Chem. Int. Ed., 2013, 52, 11257-11260.

Wickens et al., "Catalyst-Controlled Wacker-Type Oxidation: Facile Access to Functionalized Aldehydes", J. Am. Chem. Soc., 2014, 136, 890-893, Publication Online: Jan. 6, 2014.

Wickens et al., "Catalyst-Controlled Wacker-Type Oxidation: Facile Access to Functionalized Aldehydes", Organic Letters, 2012, 14, 5728-5731.

Steilmann et al, "Formation of 2-Phenylethanol From Styrene In The Presence of Zeolites and Uv Irradiation", Chem. Commun. Mar. 1999, 697-698.

Trost, "On Inventing Reactions for Atom Economy", Acc.Chem. Res., 2002, 35(9), 695-705, Publication Online: Mar. 8, 2002.

Tsuji et al., "A General Synthetic Method for the Preparation of Metyl Ketones From Terminal Olefins: 2-Decanone", Organic Syntheses, 1984, 62, 9.

FIG. 1A – PRIOR ART
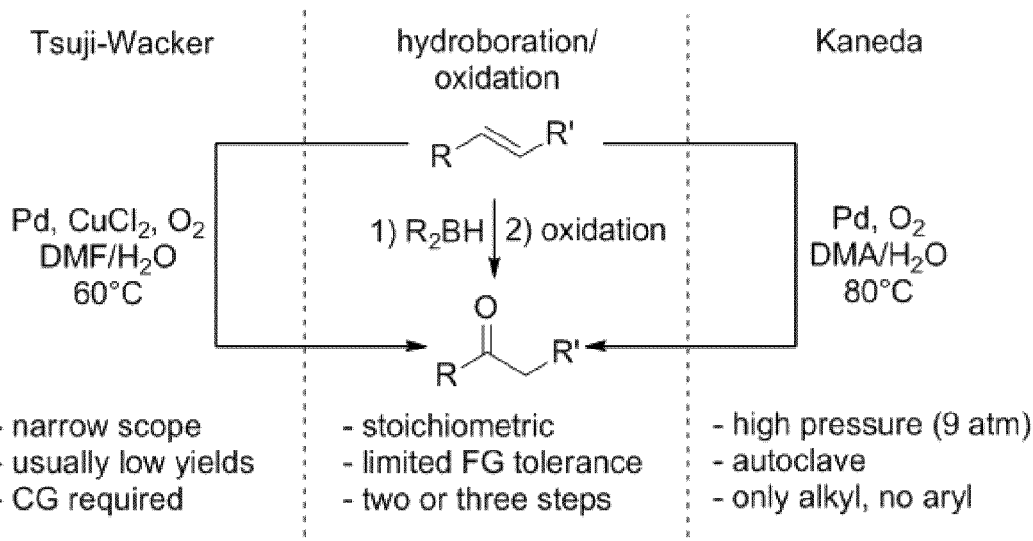
FIG. 1B – THIS WORK
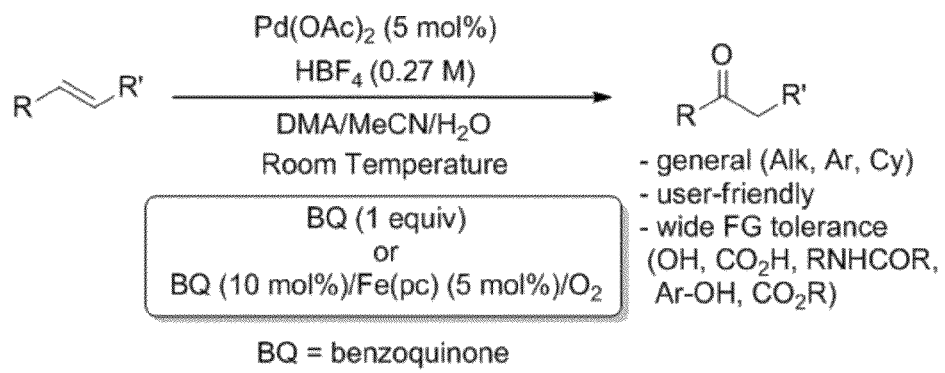
FIG. 2
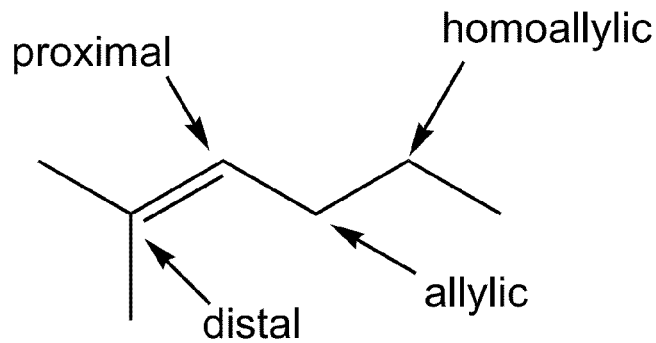

PROCESS FOR THE SYNTHESIS OF KETONES FROM INTERNAL ALKENES

CROSS REFERENCE TO RELATED APPLICATIONS

This application claims the benefit of U.S. Patent Application Ser. No. 61/750,958, filed Jan. 10, 2013, which is incorporated by reference in its entirety.

GOVERNMENT RIGHTS

This invention was made with government support under GM068825 awarded by the National Institutes of Health. The government has certain rights in the invention.

TECHNICAL FIELD

The subject matter of this invention relates to the palladium catalyzed oxidation of internal olefins to ketones.

BACKGROUND

Ketones are ubiquitous chemical entities across the molecular sciences. They serve as versatile intermediates in target-oriented synthesis, are present in a wide range of natural products and drugs, are valuable industrial products and mediate important biochemical pathways. A simple catalytic oxidation of internal alkenes under ambient conditions would therefore represent a powerful synthetic tool to access valuable ketones, since simple internal olefins are easily accessible from petroleum and renewable resources such as seed oils. Additionally, well-established synthetic routes exist to access more functionalized internal alkenes, such as carbonyl olefination and olefin metathesis. Due to the lack of an efficient catalytic transformation to synthesize ketones from internal olefins, the hydroboration/oxidation sequence is still commonly used, particularly in target-oriented synthesis. A major drawback of this procedure is the low functional group ("FG") compatibility of highly reactive borane reagents, as well as the inherent stoichiometric and multistep nature of the process (see, e.g., FIG. 1A). A direct, catalytic methodology to perform this transformation would be highly desirable. A well-studied catalytic transformation to access methyl ketones from terminal olefins is the Tsuji-Wacker reaction, though the success of the transformation is highly substrate-dependent, as shown by the variable reported yields. These aspects considerably limit the scope of the transformation. More recently, Kaneda disclosed an elegant oxygen-coupled, copper-free Wacker oxidation of internal olefins (see, e.g., FIG. 1A). This protocol shows improved substrate scope, but requires the use of high oxygen pressures (initial application of 9 atm pressure followed by 3 atm) and special equipment (autoclave). This limits its application. Therefore, the development of a general and convenient catalyzed oxidation of internal olefins to access ketones is still an unmet challenge in catalysis.

The present invention is directed to solving some of these challenges (FIG. 1B).

SUMMARY

Various embodiments of the present invention provide methods for oxidizing olefins, each method comprising contacting an organic substrate, having an initial internal olefin, with a mixture of (a) a biscationic palladium salt; and (b) an oxidizing agent; dissolved or dispersed in a solvent system to form a reaction mixture, said solvent system comprising at least one $C_{2-6}$ carbon nitrile and optionally at least one secondary alkyl amide, said method conducted under conditions sufficient to convert at least 50 mol % of the initial internal olefin to a ketone, said ketone positioned on a carbon of the initial internal olefin.

The methods allow for the variation of a number of functional parameters. In some embodiments, for example, the initial internal olefin is characterized in terms of allylically or homoallylically functionalized or allylically or homoallylically non-functionalized. Different of these olefin classes respond differently to different solvent character and these differences are described herein.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 1A summarizes the literature precedents for Wacker type olefin oxidations.

FIG. 1B illustrates an embodiment of the present invention.

FIG. 2 illustrates the concepts of terms used herein.

DETAILED DESCRIPTION OF ILLUSTRATIVE EMBODIMENTS

Figure 3A:
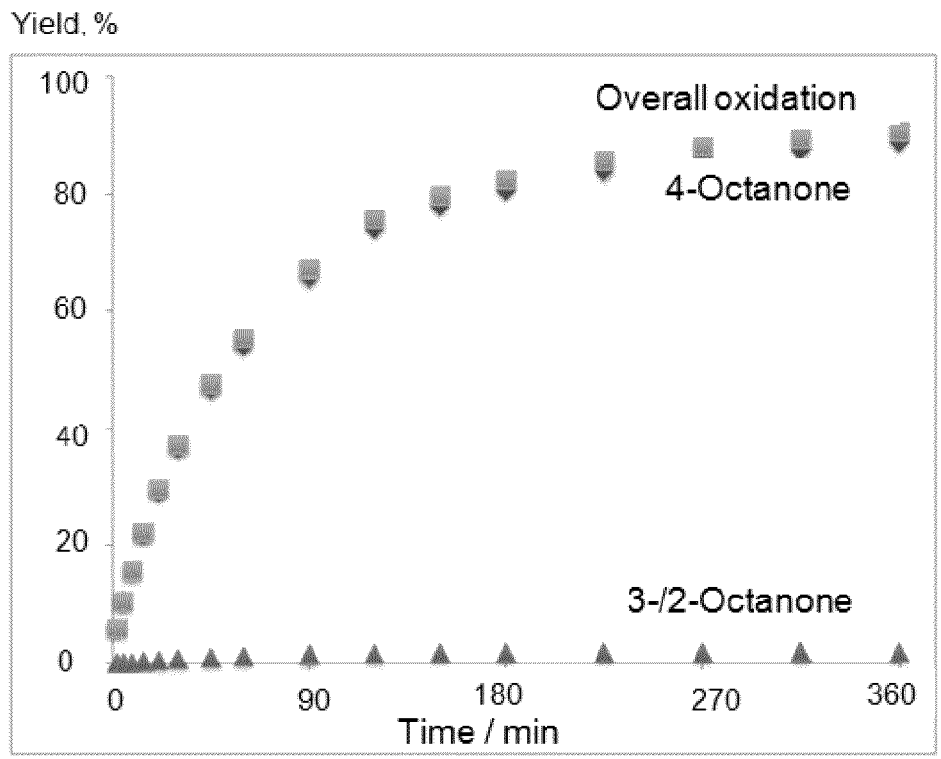
FIG. 3A illustrates the reaction progress using trans-4-octene as substrate, as described in Example 4.2.2.

The present invention is directed to a simple catalytic method for the preparation of ketones from a broad range of internal olefins. The method is tolerant to a wide range of functional groups (alcohol, acid, aldehyde, ester, phenol, amide, alkyl, aryl, cyclic). The process requires a simple palladium complex, inexpensive oxidants, dilute acid and proceeds under ambient conditions. Alternatively, the reaction can be scaled-up and coupled to oxygen at low pressures as a terminal oxidant using a biomimetic triple catalytic system.

The present invention may be understood more readily by reference to the following description taken in connection with the accompanying Figures and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and methods of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," the basic and novel characteristic(s) is the facile operability of the methods (or the systems used in such methods or the compositions derived therefrom) to regioselectively oxidize olefins under mild conditions.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C." Similarly, a subscript description for carbons or ring structures, such as $C_{1-6}$ alkyl, is understood to include each individual element of that list, and every combination of that list, as a separate embodiment, for example $C_1$-alkyl, $C_2$-alkyl, $C_3$-alkyl, $C_4$-alkyl, $C_5$-alkyl, $C_6$-alkyl, $C_{1-2}$-alkyl, $C_{1-3}$-alkyl, $C_{1-4}$-alkyl, $C_{1-5}$-alkyl, $C_{1-6}$-alkyl, $C_{2-3}$-alkyl, $C_{2-4}$-alkyl, $C_{2-5}$-alkyl, $C_{2-6}$-alkyl, $C_{3-4}$-alkyl, $C_{3-5}$-alkyl, $C_{3-6}$-alkyl, $C_{4-5}$-alkyl, $C_{4-6}$-alkyl, and $C_{5-6}$-alkyl.

Various embodiments of the present invention provide methods for oxidizing olefins, each method comprising contacting an organic substrate, having an initial internal olefin, with a mixture of (a) a biscationic palladium salt; and (b) an oxidizing agent; a dissolved or dispersed in a solvent system to form a reaction mixture, said solvent system comprising at least one $C_{2-6}$ carbon nitrile and optionally at least one secondary alkyl amide, said method conducted under conditions sufficient to convert at least 50 mol % of the initial internal olefin to a ketone, said ketone positioned on a carbon of the initial internal olefin.

The methods of the present invention are described in terms of internal olefins, because these types of olefins are traditionally more difficult to oxidize, but these methods are also effective on terminal olefins. Indeed, separate embodiments also provide that the methods and catalyst systems are applied to terminal olefins. The terms "internal" and "terminal" olefins are well understood by those skilled in the art of organic chemistry and need not be defined further here.

The substrate olefins may also be described in terms of being "allylically functionalized" and "allylically non-functionalized" (or "allylically unfunctionalized"). Unless otherwise stated, these terms refer to the presence or absence of at least one functional group comprising a heteroatom on a carbon allylic to the internal olefin. The presence of such groups appears to "guide" the placement of the eventually formed carbonyl group on one of the original olefin carbons. Additional embodiments also provide that the olefins may be "homoallylically functionalized," such that at least one functional group comprising a heteroatom is positioned on a homoallylic carbon (i.e., one more $CH_2$ away from the target olefin than the allylic carbon). See, e.g., FIG. 2.

The catalysts of the present system comprise palladium and are preferably biscationic palladium complexes in the reaction system. That is, the added catalyst contains a coordinated palladium salt, where the palladium moiety carries a formal charge of +2, said charge being balanced by the presence of anions that are poorly coordinating or non-coordinating to palladium in the solvent system, under the reactions conditions, or both. The artisan skilled in the art of organometallic chemistry would appreciate and recognize those ligands that are deemed to be poorly coordinating or non-coordinating to palladium as described herein. But, for the sake of additional clarity, some exemplary anions associated with the biscationic palladium complexes and useful for the present purpose include, but are not limited to, tetrafluoroborate anions, tetraalkylborate anions, tetraarylborate anions, mixed fluoro/alkyl/aryl-borate anions, perchlorate anions, or hexafluorophosphate anions. Where present, the alkyl groups present in a mono-, di-, tri-, or tetraborate anions may individually comprise optionally substituted linear or branched $C_{1-6}$ moieties. Tetrafluoroborate anions ($BF_4^-$) appear to be especially suitable for this purpose.

The biscationic palladium complexes may be at least partially soluble in the solvent system in the solvent system—e.g., at least about 10 wt %, at least about 25 wt %, at least about 50 wt %, or at least about 75 wt % of the added palladium complex dissolves in the reaction mixture, relative to the total weight of palladium complex added). Preferably, the palladium complex is completely dissolved in at least the solvent system and preferably completely dissolved in the reaction mixture (i.e., solvent system plus substrate) under the reaction conditions. The palladium complex may also be tethered to a non-soluble or poorly soluble organic or inorganic polymer backbone or surface, such that the method is operated heterogeneously, provided that a sufficient amount the biscationic palladium is dissolved or solvated in the solvent or reaction mixture.

The methods described herein are effective when the palladium is present in reaction mixture in a concentration in a range of from about 1 mol % to about 10 mol %, relative to the amount of internal olefin, though reaction not apparently limited to these ratios. Lower concentrations may be employed, though the conversion rates may be compromised. Higher concentrations may also be used, but at the expense of cost and subsequent palladium removal challenges.

The biscationic palladium complex may be added to the reaction solvent or mixture as such, or may be generated in situ, for example, by the reaction between a palladium carboxylate complex with the Brønsted acid of the poorly coordinating or non-coordinating anion. In this capacity, the admixture of palladium acetate with $HBF_4$ in the solvent system described herein, results in the effective formation of $Pd(MeCN)_4(BF_4)_2$, which is shown to work extremely well in these systems. In this case, it appears the generating the $Pd(MeCN)_4(BF_4)_2$ in situ, with the presence of excess protic acid yields a catalyst system with higher activity than when $Pd(MeCN)_4(BF_4)_2$ is used without the presence of excess protic acid (see, e.g., Table 1, comparing lines 2-3 with lines 4-9)

As described above, the present inventions use a solvent system comprising at least one $C_{2-6}$ carbon nitrile and optionally at least one secondary alkyl amide. As described elsewhere, the term "optionally" as in "optionally [comprising] at least one secondary alkyl amide" is intended to connote that the at least at least one secondary alkyl amide means that the alkyl amide may or may not be present, and separate embodiments account for each possibility. While the methods are operable both in the presence or absence of this co-solvent, as described herein, the magnitude of the benefit of the absence or presence of this optional solvent depends on the nature of the internal olefin substrate. The solvent system may also further comprise free protic acid, as described elsewhere herein While not intending to be bound by the correctness of any particular theory, the at least one $C_{2-6}$ carbon nitrile of the solvent system appears to serve at least two purposes. First, the nitrile functional group provides good stabilization of the biscationic palladium moiety and modulate its catalytic activity in a manner convenient to its use under mild conditions (e.g., as a $Pd(nitrile)_4^{2+}$ species). Second, the solvent helps dissolve the olefin substrates in a manner also conducive to good reactivity under mild conditions. Exemplary $C_{2-6}$ carbon nitrile include acetonitrile, propionitrile, butyronitrile, and valeronitrile, though preferred embodiments include those where the nitrile comprises or consists of acetonitrile. Again, higher alkyl nitriles or even aryl nitriles may be used, but the higher carbon character of these solvents would be expected to compromise the catalytic activities of the system(s).

The presence of an optional secondary alkyl amide appears to be especially useful when the substrates contain allylically or homoallylically non-functionalized olefins, especially allylically or homoallylically non-functionalized internal olefins. In such cases, the presence of the secondary alkyl amide appears to substantially reduce or even practically eliminate isomerization of the initial olefin position during the practice of the methods. Exemplary embodiments include those where the at least one alkyl amide comprises or consists of N-methyl pyrrolidone (N-methyl-γ-butyrolactam), N-methyl-δ-valerolactam, N,N-dimethylacetamide, or a mixture thereof. Again, the choice of the appropriate alkyl amide appears to balance the reactivity based on catalytic activity and reactant solubility. In this regard, N,N-dimethylacetamide ("DMA") is a preferred option.

Interestingly, the reactivity (conversion) and selectivity of the methods are sensitive to the relative volume ratios of the nitrile to amide solvents. Where used, for example in the conversion of allylically non-functionalized olefins, individual embodiments provide that the ratio of the nitrile to amide solvent(s) is preferably in a range of from about 0.65:1 to about 1:0.65; from about 0.7:1 to about 1:0.7; from about 0.75:1 to about 1:0.75; from about 0.8:1 to about 1:0.8; from about 0.85:1 to about 1:0.85; from about 0.9:1 to about 1:0.9; from about 0.95:1 to about 1:0.95; or about 1:1. In preferred embodiments using acetonitrile and DMA, the volume ratios are in a range of from about 0.9:1 to about 1:0.9; from about 0.95:1 to about 1:0.95; or about 1:1, with 1:1 being most preferred.

By contrast, when converting allylically functionalized internal olefins, and to some extent homoallylically functionalized olefins, the presence of the amide co-solvents substantially reduces conversion rates, and methods seeking to convert substrates containing these types of allylically or homoallylically functionalized internal olefins are best done with reduced secondary amide content, preferably substantially free of said secondary amide co-solvents. Unless otherwise stated, the term "substantially free of secondary amide" refers to a condition where the amount of amide is less than 5 vol % of the total solvent system; other embodiments provide that this term refers to less than 1 vol % or is not deliberately added to the solvent system.

In some embodiments, the solvent system further comprises water. In some embodiments, the adventitious water content in the acetonitrile or DMA is sufficient. Most of the experiments conducted with these systems and presented herein were done in the presence of about 15 vol % water, relative to the total volume of the solvent system. But the methods appears to tolerate water well, and individual embodiments provide that water be present in the solvent system in a range having a lower value of 1 vol %, 5 vol % or 10 vol % and having an upper range value of 50 vol %, 40 vol %, 30 vol %, 25 vol %, or 20 vol %.

The oxidizing agent(s) of the present methods include stoichiometric (e.g., quinones) or catalytic (e.g., comprising transition metals and oxygen) oxidizing agents.

In certain embodiments, the oxidizing agent comprises an optionally substituted quinone. When such quinones are used, the methods may be conducted aerobically or anaerobically (or any combination thereof during the course of the reaction), and are preferably substantially free of any transition metal other than the biscationic palladium catalyst. That is, except for the palladium, the reactions are conducted in the substantial absence of other transition metals historically employed in Wacker type chemistries, including Fe, Mn, and especially Cu. Exemplary quinones useful in the present invention include, but are not limited to, optionally substituted anthroquinones, optionally substituted benzoquinones, optionally substituted naphthoquinones, optionally substituted quinoline-5,8-diones, or optionally substituted isoquinoline-5,8-diones.

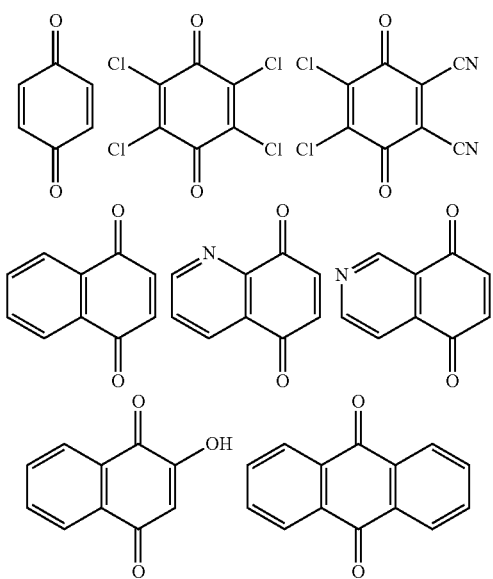

Benzoquinone is preferred, if only for convenient availability and cost.

In those embodiments when present the optionally substituted quinone is used, the quinone may be present at a stoichiometric molar ratio of quinone to internal olefin in a range of from about 0.01, about 0.1, or about 0.5 to about 1, about 1.1, or about 1.2. The lower values reflect the ability to use quinones in combination with catalytic oxidizing agents. When used without such catalytic agents, the quinones are best present at a stoichiometric molar ratio of quinone to internal olefin in a range of from about 0.9 to about 1.1, preferably in a range of about 0.95 to about 1.05. Whether used with or without catalytic oxidizing agents, the use of quinones at ratios in excess of 1.1 (for example to about 1.2, about 1.5, about 2, or about 5) is tolerated but not apparently necessary.

In certain embodiments, the oxidizing agent comprises a transition metal salt (preferentially iron or cobalt phthalacyanine) and the reaction mixture is in contacted with oxygen having a partial pressure in a range of from about 0.2 to about 2 atmospheres. In preferred embodiments, oxygen is employed at a partial pressure of about 1 atmosphere. The present methods are distinguished, even from other Wacker-type systems requiring high pressures of oxygen oxygen, by the much lower oxygen partial pressures that can be used effectively.

The methods of the present invention show remarkable conversions and selectivity at relatively mild operating conditions. For example, in some embodiments, the biscationic palladium salt is sufficiently active such at least 50 mol % of the internal olefin is converted into the corresponding ketone at a temperature in a range of about 10° C. to about 60° C. within 16 to 24 hrs. Some of the catalyst systems are more or less active to specific olefins, such that a wider array of operating conversions and yields may occur over higher and lower temperatures over longer and shorter times. For example, in some embodiments, the corresponding conversions occur at a temperature range of from about 10°, 15°, or 20° C. to about 20°, 25°, 30°, 40°, 50°, or 60° C.; preferable operating temperatures are in a range of about 15° C. to about 40° C.; or about 20° C. to about 25° C. (e.g., ambient room temperature). Lower temperatures tend to provide lower conversion rates; higher temperatures, while accelerating conversion rates, in some cases, also increase the rate of isomerization of the initial olefinic bonds, thereby compromising selectivity. It is generally possible to obtain conversions such that individual embodiments provide conversion such that the ketone group forms on one or both carbons of the original olefinic double bond in yields of at least 50%, at least 60%, at least 70%, at least 75%, at least 80%, at least 85%, at least 90%, or at least 95%, relative to the initial amount of internal olefin in the system, reflecting lack of substantial isomerization in the system during these conversions. As can be seen in the Examples, conditions may be chosen, based on the teaching herein, to provide that the ketone forms on one or both carbons of the original olefinic double bond in yields of at least 90%, or at least 95%, relative to the initial amount of internal olefin in the system.

Moreover, depending on the nature of the substrate olefin, it is possible to direct the formation of the ketone moiety to one of the olefinic carbons with great selectivity. As is shown in the Examples, the product ketone group tends to form in approximately equal amounts on either of the original olefinic carbons of allylically non-functionalized internal olefins, when the reactions are conducted in solvents containing both nitrile and secondary alkyl amides, especially acetonitrile and DMA. See, e.g., Table 2, lines 6-7, 12-14. However, when the internal olefin is allylically functionalized, a significantly greater partitioning of the position of the final ketone moiety can be obtained, especially when the solvent system is substantially free of the secondary amide co-solvent.

As used herein, unless otherwise stated, the internal olefin of the organic substrate is deemed to be "allylically functionalized" or "homoallylically functionalized" when at least one functional group comprising a heteroatom is positioned on a carbon allylic or homoallylically to the internal olefin, respectively. See FIG. 2. Such heteroatoms may comprise halo (including fluoro, chloro, bromo, or iodo, preferably fluoro), N, S, or O. The allylic positioned functional group may comprise, for example, halogen, —CF($C_{1-6}$ alkyl)$_2$, —CF$_2$($C_{1-6}$ alkyl), —CF$_3$, —N—, —S—, —O—, carbonyl, or thiocarbonyl moiety; i.e., including, but not limited to, amide, optionally protected amine, carboxylate, —COOH, —C(O)O—$C_{1-6}$ alkyl, —C(O)O—$C_{1-6}$ aryl, —O—C(O)O—$C_{1-6}$ alkyl, —O—C(O)O—$C_{1-6}$ aryl, ether, optionally protected hydroxyl, thioamide, thioester, and thiol moieties. Specific examples of functional groups comprising a heteroatom are shown in Tables 2-5. By contrast, and as described above, an allylically or homoallylically non-functionalized internal olefin is defined by the absence of such an allylic or homoallylically substituent comprising a functional group having such a heteroatom, respectively.

When such a functional group comprising a heteroatom is positioned on a carbon allylic to the internal olefin, the internal olefin may be defined as proximal and distal olefin carbons, said proximal olefin carbon being positioned closer to the allylic carbon than the distal olefin carbon. See FIG. 2. Under such circumstances, the ratio of the ketone formed on the distal carbon relative to the ketone formed on the proximal carbon is at least about 10:1, preferably at least about 20:1. This upper ratio (20:1) corresponds to greater than about 95% distal and less than about 5% proximal ketone. Even higher levels of selectivity may be achieved, for example greater than 95%, greater than 98%, greater than 99%, and greater than 99.5% distal ketone, relative to the amount of distal and proximal positioning in the final product. The methods, therefore, may be also described as methods for regioselectively preparing ketones in the presence of allylic or homoallylic functionalized directing groups, using the methods described herein, to the levels just described.

An intermediate condition may also exist, when at least one functional group comprising a heteroatom is positioned on a carbon homoallylic to the internal olefin (i.e., one more $CH_2$ away from the olefin than the allylic position. See FIG. 2. Such substrates may be said to comprise homoallylic functionalization, and may be expected methods operating on such homoallylic functionalized olefins provide ketones whose position partition in ranges intermediate between allylically non-functionalized and allylically functionalized olefins (see, e.g., Table 3, comparing lines 1 and 4 and lines 2-3 and 5).

As is shown herein, while the methods of the present invention offer flexibility of operating conditions, especially with respect to substrates, the most preferred embodiments can be described in the following terms, as depending on the nature of the substrate olefin. Such descriptions are not intended to limit the more general teachings herein.

That is, first preferred composite embodiments are those methods provide methods for oxidizing olefins, each method comprising contacting an organic substrate, having an initial internal olefin, with a mixture of (a) a biscationic palladium salt; and (b) an oxidizing agent; dissolved or dispersed in a solvent system to form a reaction mixture, said solvent system comprising at least one $C_{2-6}$ carbon nitrile and optionally at least one secondary alkyl amide, said method conducted under conditions sufficient to convert at least 50 mol % of the initial internal olefin to a ketone, said ketone positioned on a carbon of the initial internal olefin; wherein.
  (i) the organic substrate has an initial allylically or homoallylically functionalized internal olefin, said functionalization comprising at least one functional group comprising a heteroatom on a carbon allylic or homoallylic to the internal olefin, respectively, said functional group preferably comprising a halogen, —CF($C_{1-6}$ alkyl)$_2$, —CF$_2$($C_{1-6}$ alkyl), —CF$_3$, —N—, —S—, —O—, carbonyl, or thiocarbonyl moiety;
  (ii) the solvent system consists essentially of acetonitrile and water, wherein the water is present at a level of 25 vol % or less, relative to the entire volume of the solvent system;
  (iii) the biscationic palladium salt is generated in situ by the reaction of a palladium acetate complex with $HBF_4$, thereby providing a system that is sufficiently active such at least 50 mol % of the internal olefin is converted into the ketone at a temperature in a range of about 10° C. to about 60° C. within 16 to 24 hrs; and
  (iv) the oxidizing agent is either (A) benzoquinone, present at a stoichiometric molar ratio of benzoquinone to internal olefin in a range of from about 0.1 to about 1.1 or about 2.5; or (B) oxygen having a partial pressure in a range of from about 0.2 to about 2 atmospheres; or (C) both A and B.

In such preferred embodiments, the allylic or homoallylic carbon defines the internal olefin as having proximal and distal olefin carbons, said proximal olefin carbon being positioned closer to the allylic or homoallylic carbon than the distal olefin carbon, wherein the ratio of the ketone formed on the distal carbon relative to the ketone formed on the proximal carbon can be at least about 10:1, preferably at least about 20:1.

Second preferred composite embodiments are those methods provide methods for oxidizing olefins, each method comprising contacting an organic substrate, having an initial internal olefin, with a mixture of (a) a biscationic palladium salt; and (b) an oxidizing agent; dissolved or dispersed in a solvent system to form a reaction mixture, said solvent system comprising at least one $C_{2-6}$ carbon nitrile and optionally at least one secondary alkyl amide, said method conducted under conditions sufficient to convert at least 50 mol % of the initial internal olefin to a ketone, said ketone positioned on a carbon of the initial internal olefin; wherein.
  (i) the organic substrate has an initial allylically or homoallylically non-functionalized internal olefin, such that the carbon allylic or homoallylic to the internal olefin comprises only C—H, C—C, or both C—H and C—C bonds
  (ii) the solvent system consists essentially of acetonitrile, N,N-dimethyl acetamide, and water; wherein the volume ratio of the acetonitrile to the N,N-dimethyl acetamide amide solvents is in a range of from about 0.8:1 to about 1:0.8 and the water is present at a level of 25 vol % or less, relative to the entire volume of the solvent system;
  (iv) the biscationic palladium salt is generated in situ by the reaction of a palladium acetate complex with $HBF_4$, and is sufficiently active such at least 50 mol % of the internal olefin is converted into the ketone at a temperature in a range of about 10° C. to about 60° C. within 16 to 24 hrs; and
  (v) the oxidizing agent is either (A) benzoquinone, present at a stoichiometric molar ratio of benzoquinone to internal olefin in a range of from about 0.1 to about 1.1 or about 2.5; or (B) oxygen having a partial pressure in a range of from about 0.2 to about 2 atmospheres; or (C) both A and B.

In either type of the preferred composite embodiments, the biscationic palladium salt generated in situ by the reaction of $Pd(OAc)_2$ with $HBF_4$ is characterized as $Pd(MeCN)_4(BF_4)_2$.

TERMS

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Throughout this specification, words are to be afforded their normal meaning, as would be understood by those skilled in the relevant art. However, so as to avoid misunderstanding, the meanings of certain terms will be specifically defined or clarified.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and the terms "heteroatom-containing alkyl" and "heteroalkyl" refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties, or oligomeric or polymeric analogs thereof.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound to a common group such as a methylene or ethylene moiety). Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(Co)-aralkyl, wherein "alkyl," "aryl," and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo," "halide," and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Non-limiting examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

As used herein, the terms "substrate" or "organic substrate" are intended to connote both discrete small molecules (sometimes described as "organic compounds") and oligomers and polymers containing such "aromatic moieties." The term "aromatic moieties" is intended to refer to those portions of the compounds, oligomers, or polymers having an indicated aromatic structures. Where shown as structures, the moieties contain at least that which is shown, as well as containing further functionalization, substituents, or both, including but not limited to the functionalization described as "Fn" herein.

By "substituted" as in "substituted hydrocarbyl," "substituted alkyl," "substituted aryl," and the like, as alluded to in some of the aforementioned definitions, is meant that in the hydrocarbyl, alkyl, aryl, heteroaryl, or other moiety, at least one hydrogen atom bound to a carbon (or other) atom is replaced with one or more non-hydrogen substituents. Examples of such substituents include, without limitation: functional groups referred to herein as "Fn," such as halo (e.g., F, Cl, Br, I), hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo, $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH ($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$OH), sulfonate(SO$_2$O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl-SO$_2$—N(H) alkyl), $C_1$-$C_{24}$ dialkylaminosulfonyl-SO$_2$—N(alkyl)$_2$, $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (P(O)(O—)), phospho (—PO$_2$), and phosphine (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl). Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl] (DMT), methoxymethyl ether (MOM), methoxytrityl[(4-methoxyphenyl) diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-iso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline.

By "functionalized" as in "functionalized hydrocarbyl," "functionalized alkyl," "functionalized olefin," "functionalized cyclic olefin," and the like, is meant that in the hydrocarbyl, alkyl, aryl, heteroaryl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The following listing of embodiments is intended to complement, rather than displace or supersede, the previous descriptions.

Embodiment 1

A method comprising contacting an organic substrate, having an initial internal olefin, with a mixture of
(a) a biscationic palladium salt; and
(b) an oxidizing agent;
dissolved or dispersed in a solvent system to form a reaction mixture, said solvent system comprising at least one $C_{2-6}$ carbon nitrile and optionally at least one secondary alkyl amide, said method conducted under conditions sufficient to convert at least 50 mol % of the initial internal olefin to a ketone, said ketone positioned on a carbon of the initial internal olefin.

Embodiment 2

The method of Embodiment 1, wherein the at least one $C_{2-6}$ carbon nitrile comprises or consists of acetonitrile.

Embodiment 3

The method of Embodiment 1 or 2, wherein the at least one secondary alkyl amide comprises or consists of N-methyl pyrrolidone (N-methyl-γ-butyrolactam), N-methyl-6-valerolactam, N,N-dimethylacetamide, or a mixture thereof.

Embodiment 4

The method of any one of Embodiments 1 to 3, wherein the volume ratio of nitrile to amide solvents is in a range of from about 0.8:1 to about 1:0.8.

Embodiment 5

The method of any one of Embodiments 1 to 4, the solvent system further comprising water.

Embodiment 6

The method of Embodiment 5, wherein the water is present at a level of 50 vol % or less, preferably 25 vol % or less, relative to the entire volume of the solvent system.

Embodiment 7

The method of any one of Embodiments 1 to 6, the solvent system further comprising a protic acid.

Embodiment 8

The method of any one of Embodiments 1 to 7, wherein the biscationic palladium salt comprises a tetrafluoroborate anion, a tetraalkylborate anion, a tetraarylborate anion, or a mixed fluoro/alkyl/aryl-borate anion.

Embodiment 9

The method of any one of claims 1 to 8, wherein the biscationic palladium salt comprises a tetrafluoroborate anion.

Embodiment 10

The method of any one of Embodiments 1 to 9, wherein the biscationic palladium salt is generated in situ by the reaction of a palladium carboxylate complex with $HBF_4$.

Embodiment 11

The method of any one of Embodiments 1 to 10, wherein the biscationic palladium salt is $Pd(MeCN)_4(BF_4)_2$.

Embodiment 12

The method of any one of Embodiments 1 to 11, wherein the oxidizing agent is an optionally substituted quinone.

Embodiment 13

The method of any one of Embodiments 1 to 12, wherein optionally substituted quinone comprises an optionally substituted anthroquinone, an optionally substituted benzoquinone, an optionally substituted naphthoquinone, an optionally substituted quinoline-5,8-dione, or an optionally substituted isoquinoline-5,8-dione, preferably benzoquinone. Exemplary structures include:

17

-continued

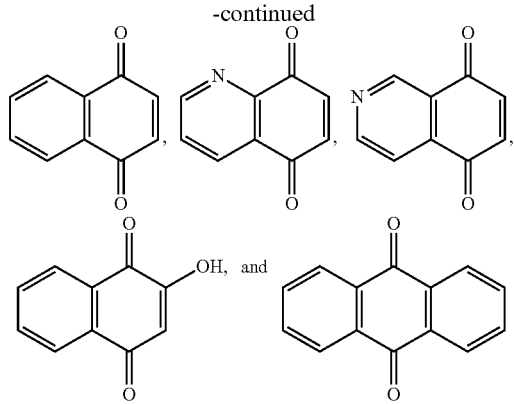

Embodiment 14

The method of any one of Embodiments 1 to 13, wherein the optionally substituted quinone, when present, is present at a stoichiometric molar ratio of quinone to internal olefin in a range of from about 0.01 to about 1.1.

Embodiment 15

The method of Embodiment 14, wherein the optionally quinone, when present, is present at a stoichiometric molar ratio of quinone to internal olefin in a range of from about 0.9 to about 1.1.

Embodiment 16

The method of any one of Embodiments 1 to 11, wherein the oxidizing agent is a transition metal salt and the reaction mixture is in contacted with oxygen having a partial pressure in a range of from about 0.2 to about 2 atmospheres.

Embodiment 17

The method of any one of Embodiments 1 to 16, wherein the biscationic palladium salt is sufficiently active such at least 50 mol % of the internal olefin is converted into the ketone at a temperature in a range of about 10° C. to about 60° C. within 16 to 24 hrs.

Embodiment 18

The method of any one of Embodiments 1 to 17, wherein at least 75% of said ketone is formed on a carbon of the internal olefin.

Embodiment 19

The method of any one of Embodiments 1 to 18, wherein the internal olefin of the organic substrate is allylically or homoallylically functionalized, said functionalization comprising at least one functional group comprising a heteroatom on a carbon allylic or homoallylic to the internal olefin, respectively.

Embodiment 20

The method of Embodiment 19, wherein the heteroatom comprises halo (preferably fluoro), N, S, or O.

18

Embodiment 21

The method of Embodiment 19 or 20, wherein the functional group comprising a heteroatom comprises a halogen, —CF($C_{1-6}$ alkyl)$_2$, —CF$_2$($C_{1-6}$ alkyl), —CF$_3$, —N—, —S—, —O—, carbonyl, or thiocarbonyl moiety.

Embodiment 22

The method of any one of Embodiments 19 to 21, wherein the allylic or homoallylic carbon defines the internal olefin as having proximal and distal olefin carbons, said proximal olefin carbon being positioned closer to the allylic or homoallyliccarbon than the distal olefin carbon, wherein the ratio of the ketone formed on the distal carbon relative to the ketone formed on the proximal carbon is at least about 10:1, preferably at least about 20:1

Embodiment 23

The method of any one of Embodiments 19 to 22, the solvent system containing essentially no secondary amide.

Embodiment 24

The method of any one of Embodiments 1 to 18, wherein the internal olefin of the organic substrate is allylically or homoallylically non-functionalized, such that the allylically or homoallylically non-functionalized internal olefin is defined by the absence of an allylic or homoallylic substituent comprising a functional group having a heteroatom, respectively.

Embodiment 25

The method of Embodiment 24, the solvent system comprising the at least one secondary alkyl amide.

Embodiment 26

The method of Embodiment 1, wherein:
(i) the organic substrate has an initial allylically or homoallylically functionalized internal olefin, said functionalization comprising at least one functional group comprising a heteroatom on a carbon allylic or homoallylic to the internal olefin, respectively, said functional group comprising a —CF($C_{1-6}$ alkyl)$_2$, —CF$_2$($C_{1-6}$ alkyl), —CF$_3$, —N—, —S—, —O—, carbonyl, or thiocarbonyl moiety;
(ii) the solvent system consists essentially of acetonitrile and water, wherein the water is present at a level of 25 vol % or less, relative to the entire volume of the solvent system;
(iii) the biscationic palladium salt is generated in situ by the reaction of a palladium acetate complex with HBF$_4$, and is sufficiently active such at least 50 mol % of the internal olefin is converted into the ketone at a temperature in a range of about 10° C. to about 60° C. within 16 to 24 hrs; and
(iv) the oxidizing agent is benzoquinone, present at a stoichiometric molar ratio of benzoquinone to internal olefin in a range of from about 0.1 to about 1.1 or about 2.5.

Embodiment 27

The method of Embodiment 26, wherein the allylic or homoallylic carbon defines the internal olefin as having proximal and distal olefin carbons, said proximal olefin carbon being positioned closer to the allylic or homoallylic carbon, respectively, than the distal olefin carbon, wherein the ratio of the ketone formed on the distal carbon relative to the ketone formed on the proximal carbon is at least about 10:1, preferably at least about 20:1

Embodiment 28

The method of Embodiment 1, wherein:
(i) the organic substrate has an initial allylically or homoallylic non-functionalized internal olefin, such that the carbon allylic or homoallylic to the internal olefin, respectively, comprises only C—H, C—C, or both C—H and C—C bonds
(ii) the solvent system consists essentially of acetonitrile, N,N-dimethyl acetamide, and water; wherein the volume ratio of the acetonitrile to the N,N-dimethyl acetamide amide solvents is in a range of from about 0.8:1 to about 1:0.8 and the water is present at a level of 25 vol % or less, relative to the entire volume of the solvent system;
(iv) the biscationic palladium salt is generated in situ by the reaction of a palladium acetate complex with $HBF_4$, and is sufficiently active such at least 50 mol % of the internal olefin is converted into the ketone at a temperature in a range of about 10° C. to about 60° C. within 16 to 24 hrs; and
(v) the oxidizing agent is either (A) benzoquinone, present at a stoichiometric molar ratio of benzoquinone to internal olefin in a range of from about 0.1 to about 1.1 or about 2.5; or (B) oxygen having a partial pressure in a range of from about 0.2 to about 2 atmospheres; or (C) both A and B.

Embodiment 29

The method of any one of Embodiments 21 to 24, wherein the biscationic palladium salt is $Pd(MeCN)_4(BF_4)_2$, generated in situ by the reaction of $Pd(OAc)_2$ with $HBF_4$.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1

Methods

All olefin oxidation reactions were carried out under aerobic conditions. Commercial reagents were obtained from Aldrich and used without further purification. $^1H$ and $^{13}C$ NMR spectra were recorded on a Varian 500 Mhz spectrometer and high resolution mass spectra were provided by the California Institute of Technology Mass Spectrometry Facility using JEOL JMS-600H High Resolution Mass Spectrometer. Gas chromatography data was obtained using an Agilent 6850 FID gas chromatography system equipped with a HP-5 (5%-phenyl)-methylpolysiloxane capillary column (Agilent). Response factors were collected for 4-octanone, 3-octanone, 2-octanone, cyclohexanone, dodecene, 2-dodecanone and lauric aldehyde following literature procedures, as described in Ritter, T.; Hejl, A.; Wenzel, A. G.; Funk, T. W.; Grubbs, R. H. *Organometallics* 2006, 25, 5740.

Example 2

General Procedure 1 (Table 1): The corresponding palladium complex (0.01 mmol, 5 mol %) and benzoquinone (21.6 mg, 0.2 mmol, 1 equiv) were charged in a resealable 4-mL vial under air. The corresponding solvent mixture was then added, followed by the addition of aqueous $HBF_4$. After the addition of trans-4-octene (22.4 mg, 0.2 mmol), the homogenous reaction mixture was stirred for 16 h at room temperature. The crude reaction mixture was then partitioned using a mixture of ether and water (10 mL each), tridecane was added as a standard, and an aliquot of the organic phase was submitted to GC-analysis to determine the yield of 4-octanone, 3-octanone, 2-octanone.

Example 3

General Procedure 2 (Table 2 and Scheme 1): Palladium acetate (11.5 mg, 0.05 mmol, 5 mol %) and benzoquinone (108 mg, 1.00 mmol) were charged in a resealable 20-mL vial under air. A mixture of DMA (2.2 mL), MeCN (2.2 mL) and water (0.63 mL) was added, followed by the addition of aqueous HBF4 (0.18 mL, 48% in water, 1.38 mmol). After the addition of the corresponding substrate (1.00 mmol), the homogenous reaction mixture was stirred for 16 h at room temperature. The crude reaction mixture was then diluted with brine (30 mL) and ether (30 mL), the phases were separated and the aqueous phase was further extracted (2×) with ether. The combined organic phases were then dried over $Na_2SO_4$, filtered, and evaporated in vacuo. In some cases, NMR-analysis of the crude mixture was performed to determine the regioselectivity of the process. The crude product was then further purified by column chromatography on silica gel using pentane/ether as eluent.

Example 4

General Procedure 3 (Scheme 2): Palladium acetate (11.5 mg, 0.05 mmol, 5 mol %), benzoquinone (10.8 mg, 0.10 mmol, 10 mol %) and Fe(phtalocyanin) (28.4 mg, 0.05 mmol, 5 mol %) were charged in a resealable 20-mL vial under air. A mixture of DMA (2.2 mL), MeCN (2.2 mL) and water (0.63 mL) was added, followed by the addition of aqueous $HBF_4$ (0.18 mL, 48% in water, 1.38 mmol). The mixture was then purged during 2 min using an oxygen balloon, and after the addition of the corresponding substrate (1 mmol), the homogenous reaction mixture was stirred for 16 h at room temperature under an atmospheric pressure of oxygen (balloon). The crude reaction mixture was then diluted with brine (30 mL) and ether (30 mL), the phases were separated and the aqueous phase was further extracted (2×) with ether. The combined organic phases were then dried over $Na_2SO_4$, filtered, and evaporated in vacuo. In some cases, NMR-analysis of the crude mixture was performed to determine the regioselectivity of the process. The crude product was then further purified by column chromatography on silica gel using pentane/ether as eluent.

Example 4.1

Octan-4-one (Table 2, Entry 1) was obtained as a clear oil (100 mg, 0.78 mmol, 78%) following the General Procedure 2. The yield obtained by GC-analysis of the crude was 87%. The difference is attributed to the high volatility of the compound. $^1$H NMR: δ 2.35 (q, J=7.0 Hz, 4H), 1.62-1.47 (m, 4H), 1.33-1.22 (m, 2H), 0.87 (td, J=7.4, 3.3 Hz, 6H). 13C NMR: δ 211.5, 44.7, 42.5, 25.9, 22.3, 17.3, 13.8, 13.7. Spectral data were in accordance with a commercial sample.

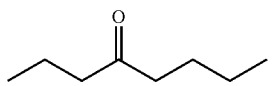

Example 4.2

Octan-4-one (Table 2, Entry 2). Cis-4-octene was reacted following the General Procedure 2. The mixture of crude products was analyzed by GC using tridecane as a standard. Yields of products: 3% 2-octanone, 3% 3-octanone, 70% 4-octanone.

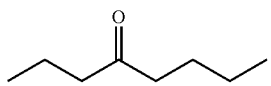

Example 4.3

Octan-2-one and octan-3-one (Table 2, Entry 3). Trans-2-octene was reacted following the General Procedure 2. The mixture of crude products was analyzed by GC using tridecane as a standard. Yields of products: 62% 2-octanone, 25% 3-octanone, 3% 4-octanone.

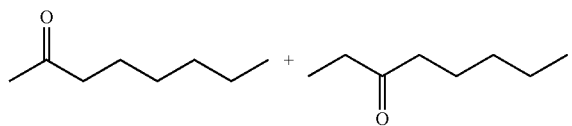

Example 4.4

Cyclohexanone (Table 2, Entry 4). Cyclohexene was reacted following the General Procedure 2. The mixture of crude products was analyzed by GC using tridecane as a standard. 75% yield was obtained. Approximately 9% cyclohexenone was observed by NMR spectroscopy using mesitylene as an internal standard.

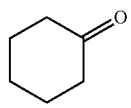

Example 4.5

1-(4-Methoxyphenyl)propan-1-one (Table 2, Entry 5) was obtained as a solid (137 mg, 0.84 mmol, 84%) following the General Procedure 2. $^1$H NMR: δ 7.92 (d, J=9.0 Hz, 2H), 6.90 (d, J=9.0 Hz, 2H), 3.83 (s, 3H), 2.92 (q, J=7.3 Hz, 2H), 1.18 (t, J=7.3 Hz, 3H). $^{13}$C NMR: δ 199.4, 163.3, 130.2, 130.0, 113.6, 55.4, 31.4, 8.4. Values were in accordance with a commercial sample.

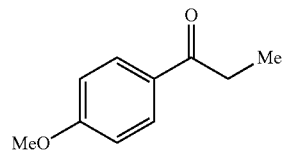 [SMILES: CCC(=O)c1ccc(OC)cc1]

Example 4.6

Propiophenone and phenyl acetone (Table 2, Entry 6) were obtained from trans-β-methyl styrene following a modified General Procedure 2 using MeCN/H$_2$O (4.4 mL/0.63 mL) as the solvent. Crude ratio by NMR was 1:1. The products could be separated by column chromatography, giving two clear oils (A: 62 mg, 0.46 mmol, 46% and B: 60 mg, 0.45 mmol, 45%). A: 1H NMR: 7.98-7.94 (m, 2H), 7.57-7.52 (m, 1H), 7.48-7.43 (m, 2H), 3.00 (q, J=7.2 Hz, 2H), 1.22 (t, J=7.2 Hz, 3H). 13C NMR: δ 200.8, 136.9, 132.9, 128.5, 128.0, 31.8, 8.2. B: 1H NMR: δ 7.36-7.32 (m, 2H), 7.30-7.25 (m, 1H), 7.23-7.19 (m, 2H), 3.70 (s, 2H), 2.15 (s, 3H). 13C NMR: δ 206.3, 134.2, 129.4, 128.8, 127.1, 51.0, 29.3. Values were in accordance with a commercial sample.

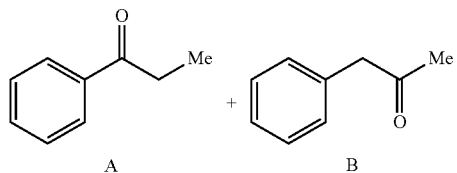

Example 4.7

Propiophenone and phenyl acetone (Table 2, Entry 7) were obtained from cis-β-methyl styrene following a modified General Procedure 2 using MeCN/H$_2$O (4.4 mL/0.63 mL) as the solvent. Crude ratio by NMR was 1.4:1 (A:B). The products could be separated by column chromatography, giving two clear oils (A: 75 mg, 0.56 mmol, 56% and B: 47 mg, 0.35 mmol, 35%). A: 1H NMR: 7.98-7.94 (m, 2H), 7.57-7.52 (m, 1H), 7.48-7.43 (m, 2H), 3.00 (q, J=7.2 Hz, 2H), 1.22 (t, J=7.2 Hz, 3H). 13C NMR: δ 200.8, 136.9, 132.9, 128.5, 128.0, 31.8, 8.2. B: 1H NMR: δ 7.36-7.32 (m, 2H), 7.30-7.25 (m, 1H), 7.23-7.19 (m, 2H), 3.70 (s, 2H), 2.15 (s, 3H). 13C NMR: δ 206.3, 134.2, 129.4, 128.8, 127.1, 51.0, 29.3. Values were in accordance with a commercial sample.

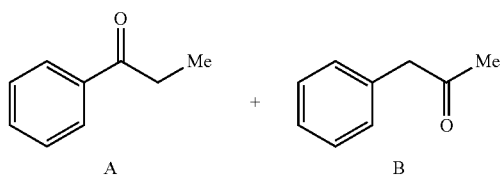

Example 4.8

3-Oxo-3-phenylpropyl acetate (Table 2, Entry 8) was obtained a as clear oil (153 mg, 0.80 mmol, 80%) following a modified General Procedure 2 using MeCN/H₂O (4.4 mL/0.63 mL) as the solvent and 10 mol % palladium acetate. ¹H NMR: δ 7.97-7.93 (m, 2H), 7.60-7.55 (m, 1H), 7.49-7.44 (m, 2H), 4.51 (t, J=6.4 Hz, 2H), 3.31 (t, J=6.4 Hz, 2H), 2.02 (s, 3H). 13C NMR: δ 197.0, 171.0, 136.5, 133.4, 128.7, 128.0, 59.6, 37.3, 20.9. Values are in accordance with literature. See *Org. Lett* 2012, 14, 2414.

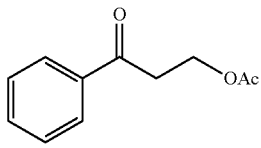 [SMILES: CC(=O)OCCC(=O)c1ccccc1]

Example 4.9

4-Oxohexyl 2-hydroxybenzoate (Table 2, Entry 9) was obtained as an oil (176 mg, 0.75 mmol, 75%) following the General Procedure 2. Crude NMR analysis showed the formation of a 4:1 mixture of regioisomers. Only the major product was isolated by column chromatography. ¹H NMR: δ 10.77 (s, 1H), 7.80 (dd, J=8.0, 1.7 Hz, 1H), 7.45 (ddd, J=8.6, 7.2, 1.7 Hz, 1H), 6.97 (dd, J=8.4, 0.8 Hz, 1H), 6.87 (ddd, J=8.2, 7.2, 1.1 Hz, 1H), 4.35 (t, J=6.4 Hz, 2H), 2.57 (t, J=7.1 Hz, 2H), 2.45 (q, J=7.3 Hz, 2H), 2.13-2.01 (m, 2H), 1.06 (t, J=7.3 Hz, 3H). ¹³C NMR: δ 210.1, 170.1, 161.7, 135.7, 129.8, 119.1, 117.6, 112.4, 64.6, 38.3, 36.1, 22.7, 7.8. HRMS (EI): calcd (M+): 236.2049; measured: 236.2046.

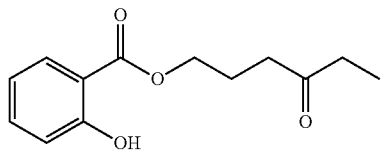 [SMILES: CCC(=O)CCCOC(=O)c1ccccc1O]

Example 4.10

4-Oxohexyl benzoate (Table 2, Entry 10) was obtained a as clear oil (200 mg, 0.91 mmol, 91%, 4:1 mixture) following the General Procedure 2. ¹H NMR: δ 8.04-7.95 (m, 2H), 7.57-7.50 (m, 1H), 7.46-7.38 (m, 2H), 4.58 (t, J=6.4 Hz, 2H, minor), 4.31 (t, J=6.4 Hz, 2H), 2.86 (t, J=6.4 Hz, 2H, minor), 2.56 (t, J=7.2 Hz, 2H), 2.44 (q, J=7.3 Hz, 2H), 2.12-1.97 (m, 2H), 1.70-1.51 (m, 2H, minor), 1.04 (t, J=7.3 Hz, 3H), 0.91 (t, J=7.4 Hz, 3H, minor). 13C NMR: δ 210.3, 207.9 (minor), 166.5, 166.4 (minor), 133.0 (minor), 132.9, 130.2 (minor), 129.5 (minor), 129.5, 128.3, 128.3 (minor), 64.2, 60.0 (minor), 45.1 (minor), 41.4 (minor), 38.6, 36.0, 22.9, 17.1 (minor), 13.7 (minor), 7.8. Values are in accordance with literature. See *Org Lett* 2011, 13, 4308.

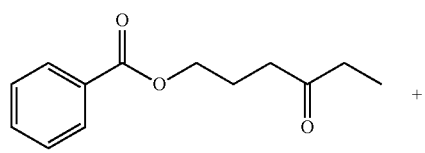

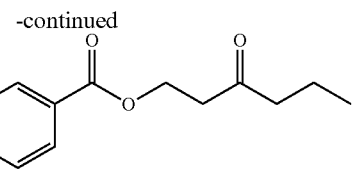

Example 4.11

1,4-Bis(benzyloxy)butan-2-one (Table 2, Entry 11) was obtained a as clear oil (150 mg, 0.53 mmol, 53%) following a General Procedure 2 using 10 mol % palladium acetate. ¹H NMR: δ 7.38-7.28 (m, 10H), 4.59 (s, 2H), 4.50 (s, 2H), 4.11 (s, 2H), 3.77 (t, J=6.2 Hz, 2H), 2.75 (t, J=6.2 Hz, 2H). 13C NMR: δ 207.0, 138.0, 137.2, 128.5, 128.4, 128.0, 127.9, 127.7, 127.7, 75.4, 73.3, 73.3, 65.0, 39.4. Values are in accordance with literature. See *Bull. Chem. Soc. Jap.* 1981, 54, 3100.

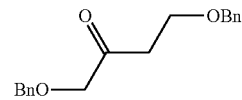

Example 4.12

10-Oxooctadecanoic acid and 9-oxooctadecanoic acid (Table 2, Entry 12) were obtained as white solids (245 mg, 0.82 mmol, 82%, 1:1) following the General Procedure 2. ¹H NMR: δ 2.37-2.33 (m, 6H), 1.66-1.49 (m, 6H), 1.35-1.20 (m, 18H), 0.86 (t, J=7.0 Hz, 3H). ¹³C NMR: δ 211.8, 211.8, 180.0, 178.0, 42.8, 42.8, 42.7, 42.7, 34.0, 34.0, 31.9, 31.8, 29.4, 29.4, 29.4, 29.3, 29.2, 29.2, 29.1, 29.0, 29.0, 29.0, 28.8, 24.6, 24.6, 23.9, 23.8, 23.7, 22.7, 22.6, 14.1, 14.1. HRMS (EI): calcd C18H34O3 (M+): 298.2508; measured: 298.2499. Values are in accordance with literature. See *Biosci. Biotechnol. Biochem* 2007, 71, 1120. *Phytochemistry* 1990, 29, 2323.

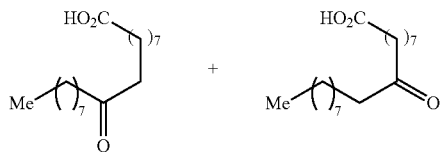

Example 4.13

Methyl 10-oxooctadecanoate and methyl 9-oxooctadecanoate (Table 2, Entry 13) were obtained as white solids (261 mg, 0.84 mmol, 84%, 1:1) following the General Procedure 2. ¹H NMR: δ 3.65 (s, 3H), 2.36 (t, J=7.5 Hz, 4H), 2.28 (t, J=7.5 Hz, 2H), 1.60-1.50 (m, J=28.6, 7.5 Hz, 6H), 1.33-1.19 (m, 18H), 0.86 (t, J=7.0 Hz, 3H). ¹³C NMR: δ 211.6, 211.6, 174.2, 174.2, 51.4, 51.4, 42.8, 42.8, 42.7, 42.7, 34.0, 34.0, 31.8, 31.8, 29.4, 29.4, 29.4, 29.3, 29.2, 29.2, 29.1, 29.0, 29.0, 28.9, 24.9, 24.8, 23.9, 23.8, 23.7, 14.1, 14.1. HRMS (EI): calcd $C_{18}H_{36}O_3$ (M⁺): 312.2664; measured: 312.2674. Values are in accordance with literature. See *Biosci. Biotechnol. Biochem* 2007, 71, 1120. *Phytochemistry* 1996, 42, 889.

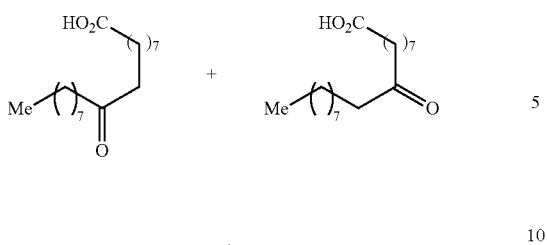
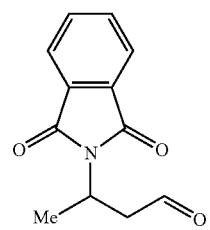

Example 4.14

18-Hydroxyoctadecan-9-one and 1-hydroxyoctadecan-9-one (Table 2, Entry 14) were obtained as white solids (215 mg, 0.76 mmol, 76%, 1:1) following the General Procedure 2. $^1$H NMR: δ 3.62 (t, J=6.6 Hz, 2H), 2.36 (t, J=7.5 Hz, 4H), 1.60-1.40 (m, 7H), 1.36-1.18 (m, 20H), 0.86 (t, J=7.0 Hz, 3H). $^{13}$C NMR: δ 211.8, 211.7, 63.0, 62.9, 42.8, 42.8, 42.8, 42.7, 32.7, 32.7, 31.8, 31.8, 29.4, 29.4, 29.4, 29.4, 29.3, 29.3, 29.3, 29.2, 29.2, 29.1, 29.1, 25.7, 25.6, 23.9, 23.8, 23.8, 22.6, 22.6, 14.1, 14.1. HRMS (EI): calcd C18H36O2 (M+): 284.2715; measured: 284.2721. Values are in accordance with literature. See *Tetrahedron* 1995, 51, 1186.

Example 4.17

N-(4-Hydroxy-3-methoxybenzyl)-8-methyl-7-oxononanamide and N-(4-hydroxy-3-methoxybenzyl)-8-methyl-6-oxononanamide (Scheme 1) was obtained as a clear oil (128 mg, 0.40 mmol, 80%, 5:1) from a mixture of capsaicin and dehydrocapsaicin (TCI, 60% capsaicin) following a modified General Procedure 2 on a 0.5 mmol substrate and using 10 mol % palladium acetate. $^1$H NMR: δ 6.83 (d, J=8.0 Hz, 1H), 6.78 (d, J=2.0 Hz, 1H), 6.73 (dd, J=8.0, 1.9 Hz, 1H), 5.96-5.89 (m, 2H), 4.31 (d, J=5.7 Hz, 2H), 3.84 (s, 3H), 2.55 (hept, J=6.9 Hz, 1H), 2.41 (t, J=7.3 Hz, 2H), 2.24 (d, J=7.0 Hz, 2H, minor), 2.18 (t, J=7.3 Hz, 2H), 2.09 (m, 2H, minor), 1.67-1.58 (m, 2H), 1.57-1.50 (m, 2H), 1.33-1.24 (m, 2H), 1.05 (d, J=6.9 Hz, 6H), 0.88 (d, J=6.6 Hz, 6H, minor). $^{13}$C NMR: δ 215.0, 210.9 (minor), 172.8, 172.5 (minor), 146.7, 145.1, 130.3, 130.2 (minor), 120.7, 114.4, 110.7, 55.9, 51.8 (minor), 43.5, 42.8 (minor), 40.8, 39.9, 36.4, 36.4 (minor), 28.7, 25.5, 25.1 (minor), 24.6 (minor), 23.2, 23.0 (minor), 22.5 (minor), 18.2. HRMS (EI): calcd for $C_{18}H_{27}NO_4$ (M+): 321.1940. found: 321.1951.

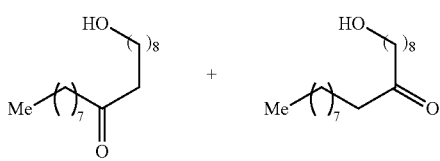

Example 4.15

Dodecan-2-one (Table 2, Entry 15) was obtained a as clear oil (158 mg, 0.86 mmol, 86%) following the General Procedure 2. GC-analysis of the crude sample showed 97.5% selectivity for ketone formation (2.5% for the aldehyde). $^1$H NMR: δ 2.39 (t, J=7.5 Hz, 2H), 2.11 (s, 3H), 1.54 (p, J=7.3 Hz, 2H), 1.30-1.15 (m, 14H), 0.86 (t, J=7.0 Hz, 3H). $^{13}$C NMR: δ 209.3, 43.8, 31.9, 29.8, 29.5, 29.4, 29.4, 29.3, 29.2, 23.8, 22.6, 14.1. Values were in accordance with a commercial sample.

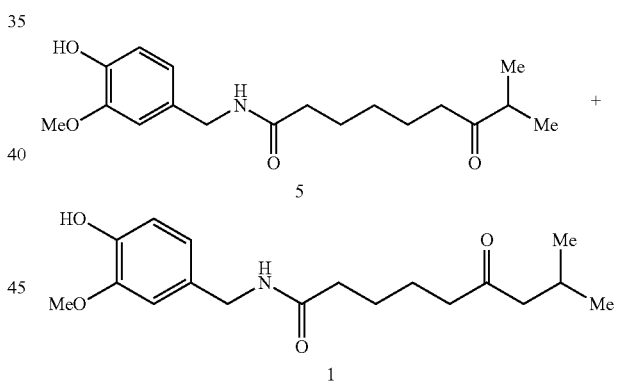

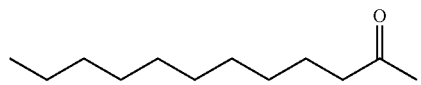

Example 4.18

Octan-4-one (Scheme 2) was obtained following the General Procedure 3. A yield of 83% was obtained by GC analysis of the crude.

Example 4.16

3-(1,3-Dioxoisoindolin-2-yl)butanal (Table 2, Entry 16) was obtained as a white solid (188 mg, 0.87 mmol, 87%) following the General Procedure 2. $^1$H NMR: δ 9.74 (s, 1H), 7.80 (dd, J=5.5, 3.0 Hz, 2H), 7.70 (dd, J=5.5, 3.0 Hz, 2H), 4.94-4.86 (m, 1H), 3.29 (ddd, J=18.0, 8.2, 1.4 Hz, 1H), 3.00 (ddd, J=18.0, 6.2, 1.1 Hz, 1H), 1.49 (d, J=7.0 Hz, 3H). 13C NMR: δ 199.3, 168.1, 134.0, 131.8, 123.2, 47.3, 41.4, 18.8. Values are in accordance with literature. See *J. Am. Chem. Soc.* 2009, 131, 9473.

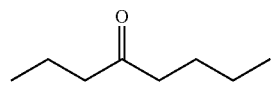

Example 4.19

1-(4-Methoxyphenyl)propan-1-one (Scheme 2) was obtained as a solid (1.59 g, 9.7 mmol, 72%) on a 2 g-scale following General Procedure 3. In that case a washing of the ethereal phase with aq. LiCl was necessary to remove DMA prior to chromatography.

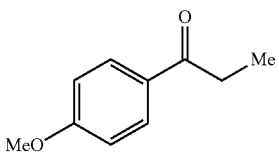

Example 4.20

10-oxooctadecanoic acid and 9-oxooctadecanoic acid (Scheme 2) were obtained as white solids (235 mg, 0.79 mmol, 79%, 1:1) following the General Procedure 3.

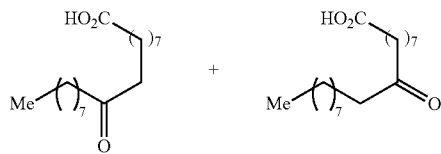

Example 4.21

Dodecan-2-one (Scheme 2) was obtained as a clear oil (140 mg, 0.76 mmol, 76%) following the General Procedure 3.

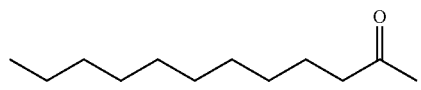

Example 4.22

Reaction profile (FIG. 3A and FIG. 3B) Each profile was generated in triplicate and the values were averaged and graphed using Microsoft Excel to produce the final curves.

Palladium acetate (11.5 mg, 0.05 mmol, 5 mol %) and benzoquinone (108 mg, 1.00 mmol) were charged into 8-mL vials with permeable septum caps under air. 5.4 mL of a stock solution consisting of all of the liquid components was added (stock solution: 9 mL MeCN, 9 mL DMA, 2 mL $H_2O$, 0.72 mL HBF4 (48% in water), 250 μL $PhNO_2$ (to be used as an internal standard) and 628 μL of either trans-4-octene or cis-4-octene (for A or B respectively)). Time points were taken at the given times and quenched with a 3:1 mixture of EtOAc and $Et_3N$, followed by analysis with GC.

Example 5

Additional Discussion on the Transformation of Allylically Non-Functionalized Olefins The methods of the present invention are attractive for a number of reasons, allowing for broad synthetic utility, among them that these methods are operated at room temperature and ambient pressure, provide for simple setup, and allow broad functional group tolerance. Initial experimental conditions used $MeCN/H_2O$ as the solvent, trans-4-octene as model substrate, palladium acetate as catalyst and benzo-quinone (BQ) as an easy to handle, inexpensive oxidant (Table 1, entry 1). Initial experiments afforded no conversion to the desired product, 4-octanone. However, on considering a biscationic palladium complex as the catalyst, it was found that the use of $Pd(MeCN)_4(BF_4)_2$ afforded nearly full conversion of the starting material to a mixture of octanone isomers (Table 1, entry 2)

TABLE 1

Optimization Studies.[a]

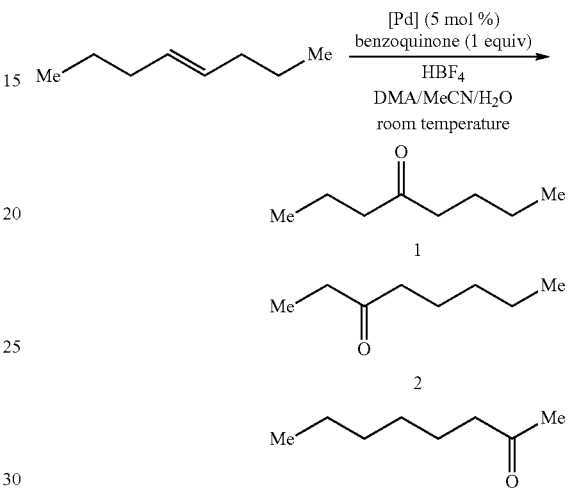

| Entry | [Pd] | HBF4 | DMA/MeCN/$H_2O$ | Yield[b] |
|---|---|---|---|---|
| 1 | Pd(OAc)$_2$ | 0 | 0/7/1 | 0(0) |
| 2 | Pd(MeCN)$_4$(BF$_4$)$_2$ | 0 | 0/7/1 | 37(41) |
| 3 | Pd(MeCN)$_4$(BF$_4$)$_2$ | 0 | 3.5/3.5/1 | 26(1) |
| 4 | Pd(MeCN)$_4$(BF$_4$)$_2$ | 0.27M | 3.5/3.5/1 | 81(3) |
| 5 | Pd(OAc)$_2$ | 0.27M | 3.5/3.5/1 | 87(2) |
| 6 | Pd(OAc)$_2$ | 0.27M | 7/0/1 | 32(6) |
| 7 | Pd(OAc)$_2$ | 0.27M | 0/7/1 | 89(8) |
| 8 | Pd(OAc)$_2$ | 0.13M | 3.5/3.5/1 | 69(2) |
| 9 | Pd(OAc)$_2$ | 0.4M | 3.5/3.5/1 | 84(3) |

[a]0.2 mmol substrate, 16 h.
[b]Yield of 4-octanone in % obtained by GC using tridecane as a standard, yields in parentheses represent the combined yield of 2 and 3 in %.

The low yield of 4-octanone appeared to be due to rapid competing isomerization of the double bond under these conditions, resulting in extensive formation of 3- and 2-octanone. The addition of DMA as a co-solvent almost completely suppressed isomerization, but resulted in only low conversion of starting material (Table 1, entry 3). In order to increase the reactivity of this system, a wide range of additives, including non-coordinating acids, were evaluated. Addition of HBF4 afforded full conversion to the desired product, 4-octanone, with only traces of the two other isomers (Table 1, entry 4). The use of $Pd(OAc)_2$ as catalyst resulted in an even improved yield under the same conditions (Table 1, entry 5). While not being bound by the correctness of any particular theory, it is likely that a similar biscationic complex is generated in situ in the presence of HBF4 via protonation of the acetate ligands. Control reactions showed that the use of a binary DMA/$H_2O$ solvent mixture afforded a lower conversion and, surprisingly, increased formation of the isomers (Table 1, entry 6). The MeCN/$H_2O$ solvent system resulted in high conversion with increased isomerization (Table 1, entry 7). Deviation from the ideal 1:1 ratio of DMA/MeCN proved ineffective. More DMA did not further improve the selectivity for oxidation over isomerization, whereas more MeCN accelerated the reaction at the cost of selectivity. A synergistic solvent effect thus appeared to represent an important and unexpected aspect of this reaction. Lowering the amount of acid had a deleterious effect on conversion, while increasing it did not afford any further improvement (Table 1, entries 8-9). Use of weaker acids such as acetic acid afforded no product formation.

Simple olefins, both acyclic and cyclic, were oxidized in an efficient manner using this optimized solvent system (Table 2, entries 1-4). The system showed a remarkable tolerance to pendant substituents or configurations (alcohol, acid, aldehyde, ester, phenol, amide, alkyl, aryl, cyclic). Styrene derivatives also afforded the product in high yields. High regioselectivity for the Markovnikov product could be obtained for the methoxy-derivative (Table 2, entry 5). The electron-neutral aromatic substrate afforded a nearly 1:1 mixture of isomers, with a slight difference in regioselectivity for the trans and the cis-alkene (entries 6-7). Cinnamyl acetate, in contrast, afforded full regioselectivity for the Markovnikov product, suggesting a strong directing effect of the acetate group (Table 2, entry 8). Importantly, no benzaldehydes were obtained as side-products with styrenes (Table 2, entries 5-8), which is in contrast to the reactions using high pressure of oxygen. O-functionalized homoallylic compounds afforded good regioselectivity (4:1) for oxidation of the more distal position (Table 2, entries 9-10).

TABLE 2

Substrate Scope.[a]

$$R_1\text{—CH=CH—}R_2 \xrightarrow[\substack{HBF_4\ (0.27M) \\ DMA/MeCN/H_2O \\ \text{room temperature}}]{\substack{Pd(OAc)_2\ (5\ mol\ \%) \\ \text{benzoquinone (1 equiv)}}} R_1\text{—C(O)—CH}_2\text{—}R_2$$

| Entry | Substrate | Product | Yield[b] |
|---|---|---|---|
| 1 | Me-CH=CH-CH₂CH₂-Me | Me-CH₂-C(O)-CH₂CH₂CH₂-Me | 78 (87)[c] |
| 2 | nPr-CH=CH-nPr (cis) | Me-CH₂CH₂-C(O)-CH₂CH₂CH₂-Me | 70[c] |
| 3 | Me-CH=CH-(CH₂)₄-Me | Me-C(O)-nHex + Et-C(O)-nPen | 87[c] (2.5:1)[d] |
| 4 | cyclohexene | cyclohexanone | 75[c] |
| 5 | 4-MeO-Ph-CH=CH-Me | 4-MeO-Ph-C(O)-CH₂-Me | 84 |
| 6[e] | Ph-CH=CH-Me (trans) | Ph-C(O)-CH₂-Me + Ph-CH₂-C(O)-Me | 91 (1:1)[f] |
| 7[e] | Ph-CH=CH-Me (cis) | Ph-C(O)-CH₂-Me + Ph-CH₂-C(O)-Me | 91 (1.4:1)[f] |
| 8[e,g] | Ph-CH=CH-CH₂-OAc | Ph-C(O)-CH₂CH₂-OAc | 80 |

TABLE 2-continued

Substrate Scope.[a]

$$R_1\diagdown\!\!=\!\!\diagup R_2 \xrightarrow[\text{DMA/MeCN/H}_2\text{O}]{\substack{\text{Pd(OAc)}_2\ (5\ \text{mol \%}) \\ \text{benzoquinone (1 equiv)} \\ \text{HBF}_4\ (0.27\text{M}) \\ \text{room temperature}}} R_1\diagdown\!\!\underset{\text{O}}{\text{C}}\!\!\diagup\!\!R_2$$

| Entry | Substrate | Product | Yield[b] |
|---|---|---|---|
| 9 | 2-hydroxybenzoate ester of (Z)-hept-3-en-1-ol | 2-hydroxybenzoate ester of 4-oxohexyl | 75[h] |
| 10 | BzO-(CH₂)₃-CH=CH-Et (Z) | BzO-(CH₂)₃-C(O)-Et + BzO-(CH₂)₂-C(O)-nPr | 91 (4:1)[d] |
| 11[g] | BnO-CH₂-CH=CH-CH₂-OBn | BnO-CH₂-C(O)-CH₂-CH₂-OBn | 53 |
| 12 | HO₂C-(CH₂)₇-CH=CH-(CH₂)₇-Me (oleic acid) | HO₂C-(CH₂)₇-C(O)-CH₂-(CH₂)₇-Me + HO₂C-(CH₂)₇-CH₂-C(O)-(CH₂)₇-Me | 82 (1:1)[d] |
| 13 | MeO₂C-(CH₂)₇-CH=CH-(CH₂)₇-Me | MeO₂C-(CH₂)₇-C(O)-CH₂-(CH₂)₇-Me + MeO₂C-(CH₂)₇-CH₂-C(O)-(CH₂)₇-Me | 84 (1:1)[d] |
| 14 | HO-(CH₂)₈-CH=CH-(CH₂)₇-Me | HO-(CH₂)₈-C(O)-CH₂-(CH₂)₇-Me + HO-(CH₂)₈-CH₂-C(O)-(CH₂)₇-Me | 76 (1:1)[d] |
| 15 | Me-(CH₂)₉-CH=CH₂ | Me-(CH₂)₉-C(O)-Me | 86 |
| 16 | N-phthalimido-CH(Me)-CH=CH₂ | N-phthalimido-CH(Me)-CH₂-CHO | 87 |

[a] 1 mmol alkene, DMA/MeCN/H₂O (3.5:3.5:1), 16 h.
[b] Isolated yields in %.
[c] GC-yield using tridecane as a standard.
[d] Product ratio.
[e] MeCN/H₂O (7:1).
[f] Product ratio, isomers could be separated by CC.
[g] 10 mol % Pd.
[h] 19% of the minor isomer was present in the crude reaction mixture and was not isolate.

In light of recent growing interest for direct functionalization of renewable seed oil derivatives, unprotected oleic acid derivatives (Table 2, entries 12-14) were also examined. The method proceeded in high yield with these compounds bearing unprotected acid and alcohol functional groups.

The ability of this system to perform the oxidation of terminal olefins was also examined. Dodecene, a substrate classically prone to isomerization in traditional Wacker chemistry, afforded the desired product in high yield. Conversion of allylic phthalimides resulted in the regioselective formation of the aldehyde.

With continuing interest in testing the synthetic potential of this new transformation, its application on a poly-functionalized natural product was also considered. Capsaicin is an important compound with applications in cancer and pain relief research. The internal alkene group was smoothly oxidized in the presence of the other functional groups, affording high yield of the desired product, suggesting good utility of these methods on more complex targets. Without intending to be bound by the correctness of any particular theory of operation, the notable regioselectivity (5:1) was post-rationalized by steric repulsion in the hydroxylpalladation step between the Pd-center and the iPr-group.

Scheme 1. Oxidation of a bioactive natural product.

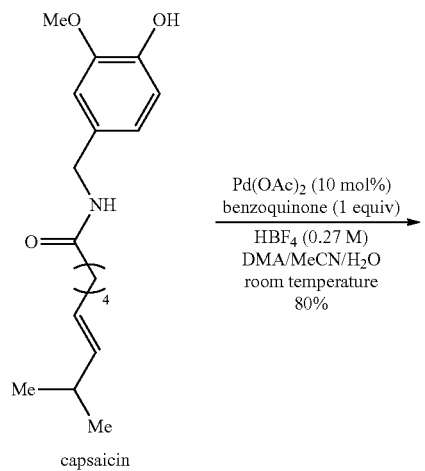

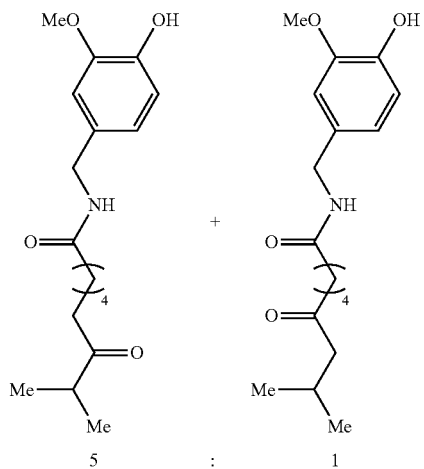

Recognizing the inherent limitation of the use of stoichiometric benzoquinone for larger-scale applications, experiments were conducted to use oxygen as terminal oxidant. Initial results using only 10 mol % benzoquinone and 5 mol % Fe(pc) (pc=phthalocyanine) mirrored the outcome of the stoichiometric process. Control experiments showed that the reaction using both the iron catalyst and benzoquinone afforded the highest yield and best prevented isomerization. Unexpectedly, catalyst turnover was also observed in the absence of redox catalysts (Scheme 2). Indeed, the reaction went nearly to completion in all three control reactions performed. Under the directly oxygen-coupled system, full conversion to a mixture of octanone isomers (16%, 20%, 31%) was obtained. While not known or predicted, this unprecedented outcome might be the result of a synergistic solvent effect. The low selectivity for 4-octanone was a result of rapid competing isomerization under these conditions. Alternatively or additionally, it is conceivable that the iron catalyst and benzoquinone suppress isomerization via the trapping of a putative palladium-hydride species. Alternatively, the redox catalysts could accelerate the rate of oxidation relative to that of isomerization. Despite the mixture of isomers obtained, this result holds great promise for the potential development of a direct oxygen-coupled oxidation of internal olefins under ambient conditions. The triple catalytic system was also to the oxidation of selected key substrates from Table 2 in good yields. The results obtained with this system bode well for larger-scale application, a feature further confirmed by the comparable yield obtained for the oxidation of trans-anethole on a 2 g-scale.

Scheme 2. Catalytic system for aerobic oxidation. [a] GC-yields using tridecane as a standard. Yields in parentheses represent the combined yield of 2 and 3. [b] Isolated yields.

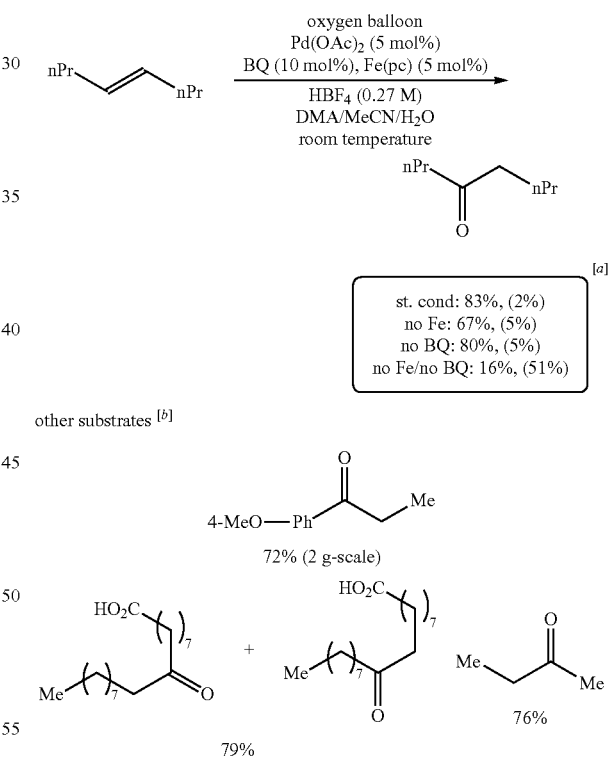

Figure 3B:
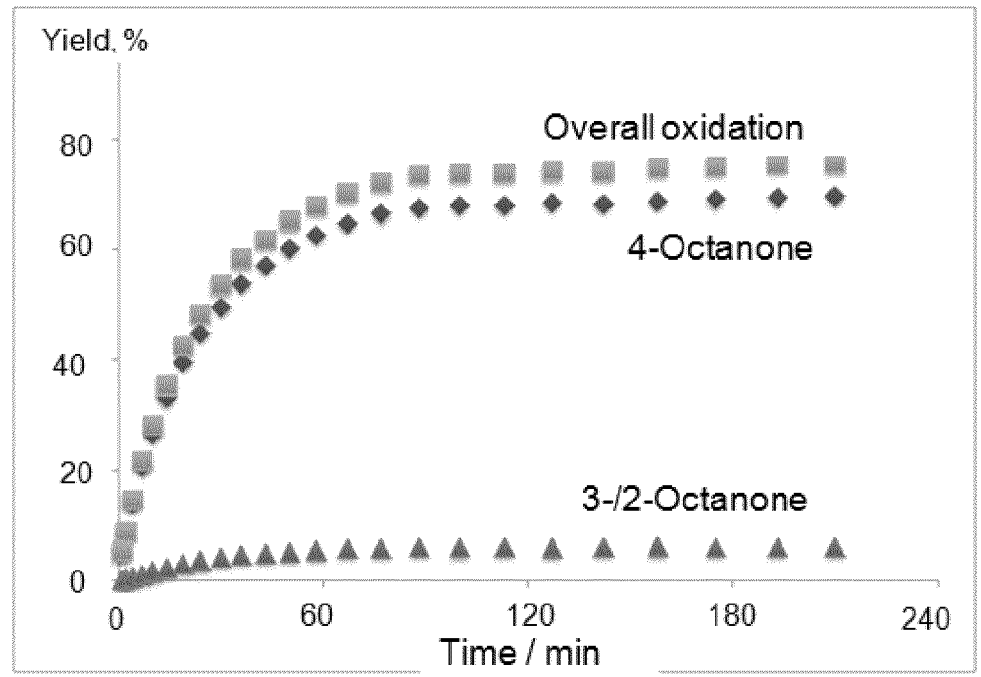
FIG. 3B illustrates the reaction progress using cis-4-octene as substrate, as described in Example 4.2.2.

Due to the scarcity of reports involving oxidation of internal olefins and the corresponding lack of mechanistic information, the progress of the reaction with stoichiometric benzoquinone and both trans-4-octene (A) and cis-4-octene (B) was tracked (See Example 4.2.2 and FIG. 3A and FIG. 3B). Oxidation of the cis-isomer was significantly faster and proceeded with slightly more isomerization than the trans-isomer. The data did not fit a simple first order rate-law, and thus seemed to indicate a more complex dependence on alkene concentration.

Example 6

Additional Discussion on the Transformation of Allylically Functionalized Olefins Additional experiments were conducted on substrates wherein an allylic heteroatom was positioned proximate to the alkene to determine the effect of such a substituent on the regioselectivity of the process. Such studies using the present catalyst systems were prompted the low yields, requiring the use of peroxide as oxidants and/or high oxygen pressure, and limited in scope of other oxidation systems with internal olefins.

isomerization in the presence of coordinating groups. Based on these preliminary results, a selection of simple mono-allylically-functionalized alkene substrates to efficiently probe the influence of diverse groups on the regioselectivity (Table 3). Allylic alcohol derivatives demonstrated that good regioselectivity could be obtained using common protecting groups, such as benzyl (Bn; 9:1). Introduction of a benzoate group increased the regioselectivity to greater than or equal to 20:1. This result is particularly interesting in light of potential known side reactions of allylic esters, such as the well-established palladium-catalyzed allylic substitution and rearrangement. For example, a recent report from Feringa and co-workers showed a strong preference for allylic rearrangement

TABLE 3

Initial Scope of Directing Groups[a]

R⁀DG + Pd(OAc)₂ (5 mol %), BQ (1 equiv), HBF₄ (0.27M), MeCN/H₂O, RT → R-C(O)-CH₂-DG

| Entry | Substrate | Product | Yield [%][b] | Sel.[c] |
|---|---|---|---|---|
| 1 | Me-(CH₂)₄-CH=CH-CH₂-OBn | Me-(CH₂)₄-C(O)-CH₂-OBn | 71 | 9:1 |
| 2 | Me-(CH₂)₄-CH=CH-CH₂-OBz | Me-(CH₂)₄-C(O)-CH₂-OBz | 80 | ≥20:1 |
| 3 | Me-CH=CH-CH(OBz)-Me | Me-C(O)-CH₂-CH(OBz)-Me | 80 | ≥20:1 |
| 4 | Me-CH=CH-CH₂-CH₂-OBn | Me-C(O)-CH₂-CH₂-CH₂-OBn | 80 | 6.5:1 |
| 5 | Me-CH=CH-CH₂-CH₂-OBz | Me-C(O)-CH₂-CH₂-CH₂-OBz | 83 | 10:1 |
| 6 | Me-CH=CH-CH₂-C(O)-OMe | Me-C(O)-CH₂-CH₂-C(O)-OMe | 70 | ≥20:1 |
| 7 | Me-CH=CH-CH₂-NHTs | Me-C(O)-CH₂-CH₂-NHTs | 72 | ≥20:1 |

[a] 1 mmol alkene, MeCN/H₂O (7:1), 16 h.
[b] Yield of isolated product.
[c] Sel. = distal oxidation/proximal oxidation. Determined by ¹H NMR analysis. DG = direction group.
Bz = benzoyl, Ts = 4-toluenesulfonyl.

Initial preliminary experiments using a solvent system optimized for oxidizing allylically non-functionalized olefins (DMA/MeCN/H₂O) led to long reaction times with incomplete conversion. For allylically functionalized substrates, the use of a binary solvent system (MeCN/H₂O) and acid led to a much more active system and full conversion was obtained. In contrast to the oxidation of allylically non-functionalized alkenes, DMA did not appear to be necessary to prevent over oxidation of internal alkenes. See, e.g., J. J. Dong, et al., *Angew. Chem.* 2013, 125, 5671; *Angew. Chem. Int. Ed.* 2013, 52, 5561. A branched allylic benzoate afforded a similar excellent result and thus bodes well for the use of more elaborated substrates (Table 3, entry 3). We then explored the ability of homoallylic functionalities to direct the oxidation reaction, since the corresponding oxidation products are not readily accessible by traditional carbon-carbon forming processes. Synthetically viable regiocontrol for the distal oxidation product was obtained with up to greater than or equal to 20:1 selectivity (Table 3, entries 4-6). Interestingly, this approach is not limited to protected alcohols, as an b,g-unsaturated methyl ester afforded the distal oxidation product 5 (Table 3, entry 6). An allylic NHTs group gave the corresponding amino-ketone derivative in high regioselectivity, thus expanding the reaction scope to nitrogen-derived directing groups (Table 3, entry 7). Overall, the methodology provides an outstanding route to hydroxyketones, aminoketones, and ketoesters.

Additional experiments were conducted to illustrate the power of a combined cross-metathesis/regioselective Wacker sequence in the preparation of hydroxy- and aminoketones (Schemes 3 and 4).

-continued

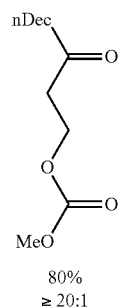

80%
≥ 20:1

Scheme 3. Sequential cross-metathesis/regioselective Wacker oxidation for the preparation of functionalized ketones.

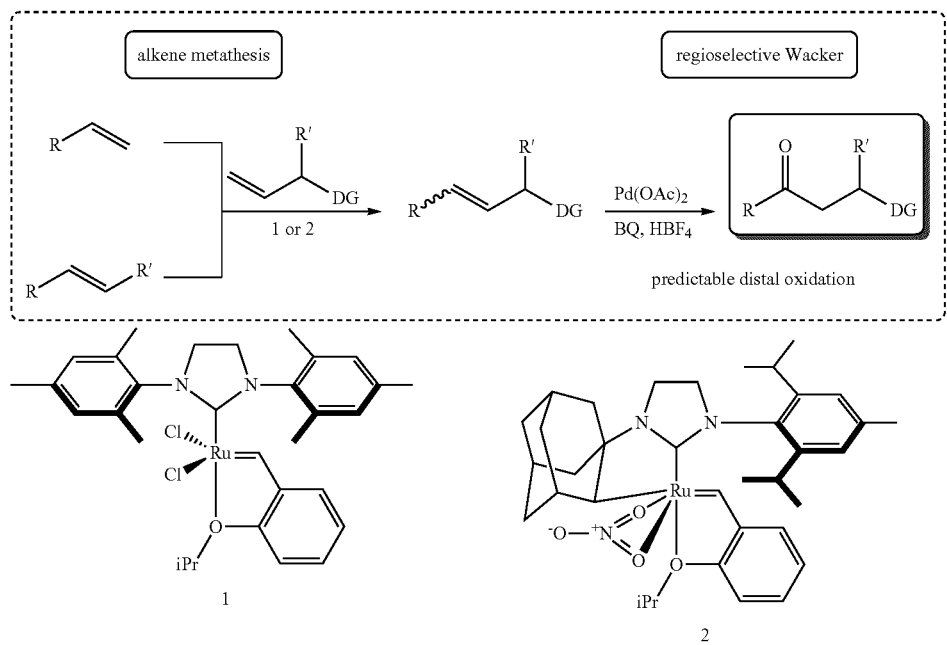

BQ = benzoquinone.

Scheme 4. Preparation and further screening of directing groups enabled by cross-methathesis.

CM/Wacker

-continued

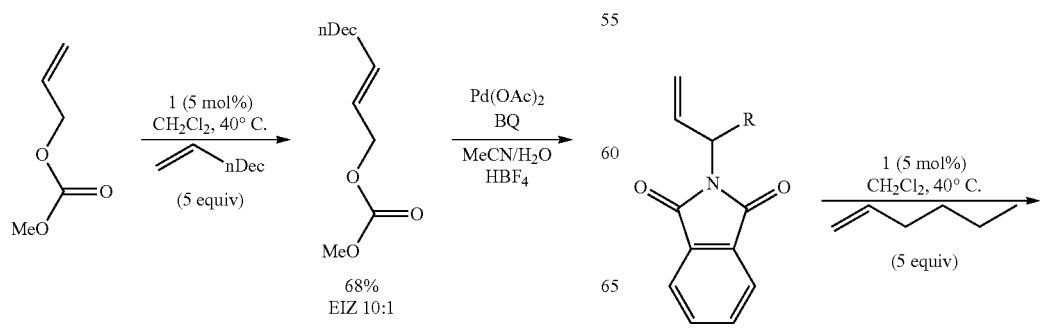

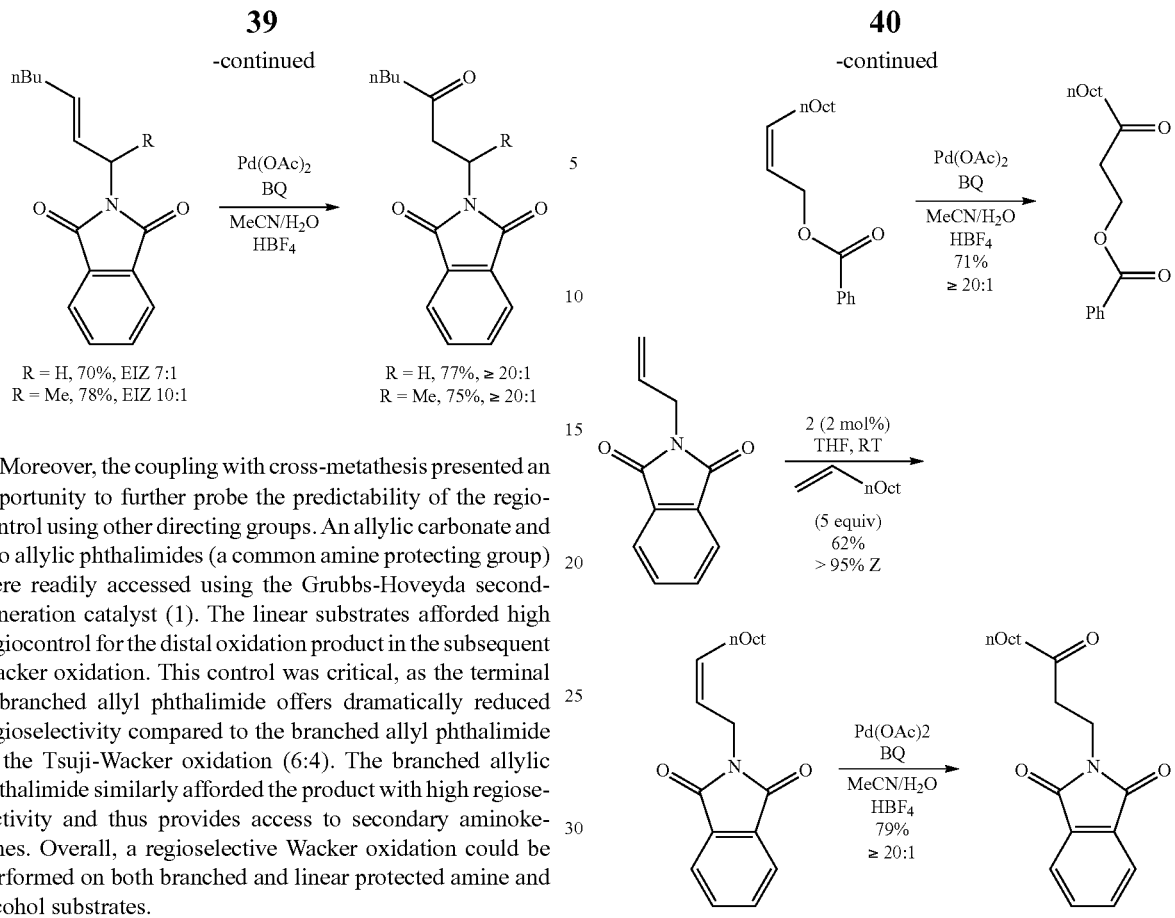

Moreover, the coupling with cross-metathesis presented an opportunity to further probe the predictability of the regiocontrol using other directing groups. An allylic carbonate and two allylic phthalimides (a common amine protecting group) were readily accessed using the Grubbs-Hoveyda second-generation catalyst (1). The linear substrates afforded high regiocontrol for the distal oxidation product in the subsequent Wacker oxidation. This control was critical, as the terminal unbranched allyl phthalimide offers dramatically reduced regioselectivity compared to the branched allyl phthalimide in the Tsuji-Wacker oxidation (6:4). The branched allylic phthalimide similarly afforded the product with high regioselectivity and thus provides access to secondary aminoketones. Overall, a regioselective Wacker oxidation could be performed on both branched and linear protected amine and alcohol substrates.

Despite recent progress in the oxidation of internal alkenes, Z alkenes have proven either inert or prone to positional isomerization in Wacker-type oxidations. Since many olefination reactions produce either Z alkenes or a mixture of both Z and E isomers, the effect of alkene geometry upon the oxidation was probed. To this end, it was critical to access the desired starting materials as stereochemically pure Z isomers to clearly understand the underlying isomeric dependence on the reaction outcome. Therefore, substrates were prepared by a new class of chelated ruthenium alkene metathesis catalysts which exhibit exquisite kinetic control to access the corresponding Z substrates (Scheme 5). See, e.g., (a) B. K. Keitz, et al., *J. Am. Chem. Soc.* 2011, 133, 9686; (b) B. K. Keitz, et al., *J. Am. Chem. Soc.* 2012, 134, 693; (c) L. E. Rosebrugh, et al., *J. Am. Chem. Soc.* 2013, 135, 1276; d) M. B. Herbert, et al., *Angew. Chem.* 2013, 125, 328; Angew. Chem. Int. Ed. 2013, 52, 310.

Scheme 5. Demonstration of an efficient regioselective Wacker oxidation of Z substrates enabled by Z-selective cross-metathesis. THF = tetrahydrofuran Z-CM/Wacker

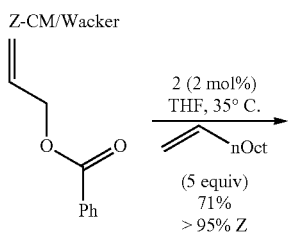

The chelated catalyst could be used to prepare the desired Z substrates cleanly from allyl benzoate and allyl phthalimide in good yields and greater than 95% Z selectivity. These two products were then smoothly transformed into the corresponding ketones in high regioselectivity and yield, comparable to the results obtained for the E isomers. These results thus establish that the efficiency of the inventive oxidation protocol towards E alkenes also applies to Z alkenes.

With an interest in further probing the synthetic utility of the metathesis/regioselective Wacker sequence, this strategy was explored in the context of the bioactive, polyfunctionalized alkene starting material capsaicin (Scheme 6a). Both steps worked in good yields, and the regioselectivity of the Wacker step proved to be as high as in the more simple examples. No interference with the directing ability of the benzoate moiety was observed, thus validating the potential of this strategy for complex-molecule functionalization. This methodology may also be used to enable rapid generation of functionalized molecules from inexpensive and renewable seed oil derivatives (Scheme 6b). Oleyl alcohol could be selectively transformed into two substituted allylic benzoate substrates using the catalyst 1. The two intermediates could further be oxidized in high selectivity to the corresponding ketones under our standard oxidation conditions.

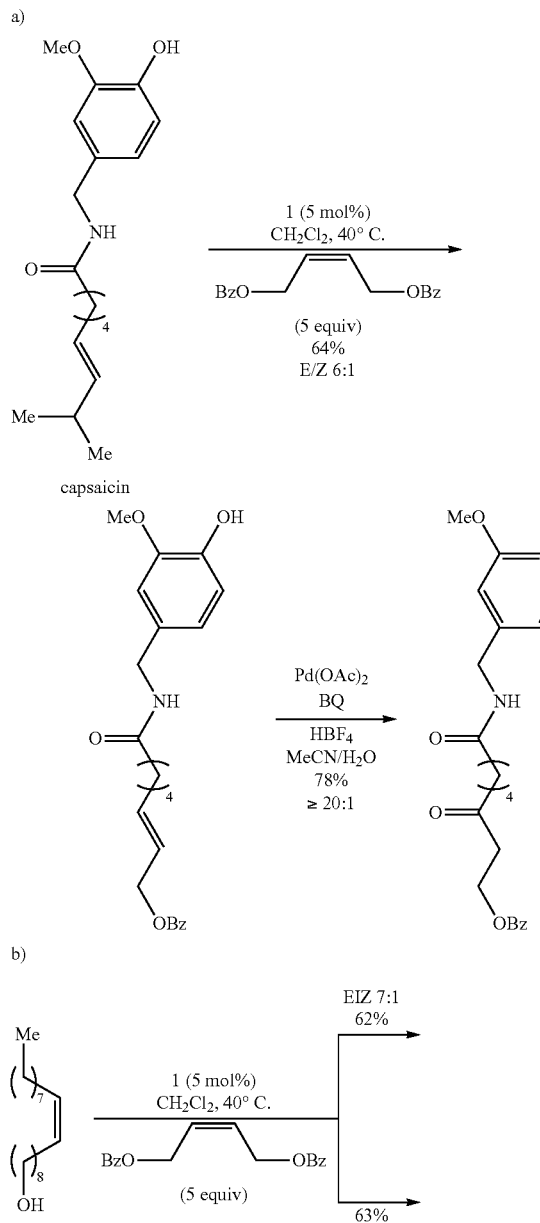

Scheme 6. Applications of the novel synthetic sequence to a polyfunctionalized target as well as in the selective functionalization of a seed oil derivative.

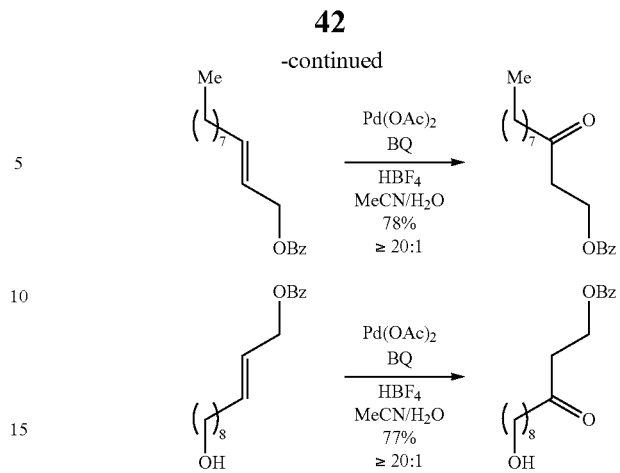

Finally, and while not necessary to support the methods as claimed, experiments were done to explore the origin of regioselectivity of the inventive protocols. It was possible to take advantage of the synthetic flexibility offered by the benzoate aromatic moiety to qualitatively study the electronic effects of the substituents on the reaction outcome. Competition experiments were performed between the allylic benzoate derivative and the corresponding 4-$NO_2$ and 4-MeO derivatives. The relative rates are shown in Scheme 7, with a rate following the order of $NO_2$<H<MeO. This long-range electronic effect suggests the significant buildup of a positive charge in the transition state. Additionally, an allylic OBn (where "Bn" is benzyl) was tested to uncover the effect of this group on the relative rate. The benzyl group is more electron-donating than the acyl substituents previously tested. This OBn substrate was oxidized with an increased rate and gave lower selectivity, and is thus consistent with the inductive trend previously observed. To further probe the effect of electron density on the relative oxidation rate, an intramolecular competition experiment using a substrate bearing both an allylic OBn and an allylic 4-$NO_2$—BzO was performed. The product from the oxidation of the most electron-rich position (distal to the 4-$NO_2$—BzO) group), was oxidized with a remarkable greater than 20:1 regioselectivity. This outcome supplemented the results of the intermolecular experiments and demonstrated that protecting-group selection can enable selective oxidation, even when potentially competing directing groups are proximal to the alkene. Benzoyl and benzyl groups are orthogonal protecting groups, and thus, this result will have significant implications in target-oriented synthesis. Overall, the observed rate and selectivity trend indicated that the regioselectivity of the process has a significant inductive component. An inductive model is also consistent with the selectivity obtained with the more electron-withdrawing benzoate as compared to the homoallylic benzyl-protected alcohol.

Scheme 7. Qualitative study of inductive effects on the relative rate and regioselectivity using both a) intermolecular and b) intramolecular competition experiments.
Yield is that of the isolated product.

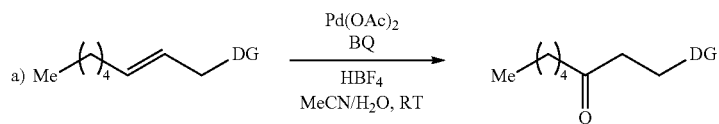

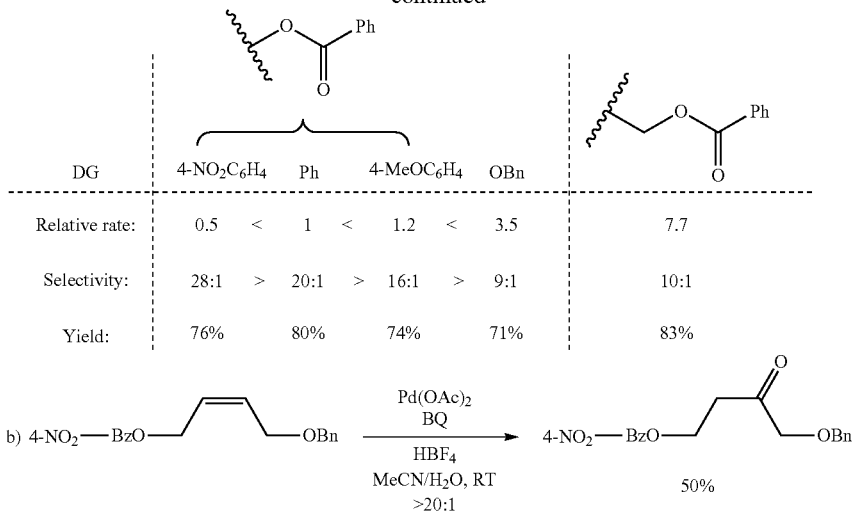

| DG | 4-NO$_2$C$_6$H$_4$ | | Ph | | 4-MeOC$_6$H$_4$ | | OBn | |
|---|---|---|---|---|---|---|---|---|
| Relative rate: | 0.5 | < | 1 | < | 1.2 | < | 3.5 | 7.7 |
| Selectivity: | 28:1 | > | 20:1 | > | 16:1 | > | 9:1 | 10:1 |
| Yield: | 76% | | 80% | | 74% | | 71% | 83% |

Overall, the high functional-group tolerance of both the cross-metathesis step and the Wacker oxidation, combined with the predictable regioselectivity of the oxidation step, holds great promise in the wide adoption of this strategy in organic synthesis.

Example 7

Additional Discussion on the Transformation of —CF$_3$ Functionalized Olefins Still further experiments were conducted to investigate the ability of allylic CF$_3$-groups to effect the oxidation of internal olefins, using the experimental protocols developed for other internal olefins. The results are shown in Table 4. As seen for the other allylically functionalized olefins, the presence of DMA seemed to provide an inhibitory effect on conversion, but no effect on selectivity. Additionally, the regioselectivity to generate the ketone on the olefin carbon distal to the CF$_3$ moiety was remarkably high.

TABLE 4

Optimization studies for the oxidation of internal olefins with an allylic CF$_3$ group[a]

| Entry | Time [h] | Temp. | MeCN/H$_2$O/DMA | Cat. (mol %) | Conversion[b] | Sel.[d] |
|---|---|---|---|---|---|---|
| 1 | 15 | rt. | 7.1:1.0:0 | 5 | 77 | ≥20:1 |
| 2 | 15 | rt. | 3.5:1.0:3.5 | 5 | 35 | ≥20:1 |
| 3 | 15 | 40° C. | 7.1:1.0:0 | 5 | 87 | ≥20:1 |
| 4 | 15 | 40° C. | 3.5:1.0:3.5 | 5 | 33 | ≥20:1 |
| 5 | 15 | 40° C. | 7.1:1.0:0 | 10 | 93 | ≥20:1 |
| 6 | 15 | 50° C. | 7.1:1.0:0 | 5 | 85 | ≥20:1 |
| 7 | 24 | 40° C. | 7.1:1.0:0 | 5 | 90 | ≥20:1 |
| 8 | 24 | 50° C. | 7.1:1.0:0 | 7.5 | 91 | ≥20:1 |
| 9 | 24 | 60° C. | 7.1:1.0:0 | 7.5 | 94 | ≥20:1 |

[a]0.1 mmol alkene, BQ = p-Benzoquinone, DMA = Dimethylacetamide
[b]As assessed by $^{19}$F-NMR of the crude reaction mixture after work-up.
[c]Yield calculated from an internal standard (α,α,α-trifluorotoluene).
[d]Sel. = distal oxidation/proximal oxidation. Determined by $^{19}$F- and $^1$H-NMR analysis.

Consistent with the results for other olefins, experiments using different pendant moieties distant from the olefin showed remarkable substituent tolerance, while maintaining extremely high selectivity for the distal olefin carbon. See Table 5.

TABLE 5

Tolerance of functional groups for the $CF_3$-directed oxidation of internal olefins[a].

[a]0.25 mmol alkene, BQ = p-Benzoquinone
[b]Preparative yields in percent. After work-up and purification by Flash Column Chromatography (diethyl ether/pentane as solvent system)
[c]0.5 mmol alkene (see biweekly report 2)
[d]Sel. = distal oxidation/proximal oxidation. Deteremined by $^{19}F$- and $^1H$-NMR analysis.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A method comprising contacting an organic substrate, having an initial internal olefin, with a mixture of
   (a) a biscationic palladium salt; and
   (b) an oxidizing agent;
dissolved or dispersed in a solvent system to form a reaction mixture, said solvent system comprising at least one $C_{2-6}$ carbon nitrile and optionally at least one secondary alkyl amide, said method conducted under conditions sufficient to convert at least 50 mol % of the initial internal olefin to a ketone, said ketone positioned on a carbon of the initial internal olefin.

2. The method of claim 1, wherein the at least one $C_{2-6}$ carbon nitrile comprises or consists of acetonitrile.

3. The method of claim 1, wherein the at least one secondary alkyl amide comprises or consists of N-methyl pyrrolidone (N-methyl-γ-butyrolactam), N-methyl-δ-valerolactam, N,N-dimethylacetamide, or a mixture thereof.

4. The method of claim 1, wherein the volume ratio of nitrile to amide solvents is in a range of from about 0.8:1 to about 1:0.8.

5. The method of claim 1, the solvent system further comprising water.

6. The method of claim 5, wherein the water is present at a level of 50 vol % or less, relative to the entire volume of the solvent system.

7. The method of claim 1, the solvent system further comprising a protic acid.

8. The method of claim 1, wherein the biscationic palladium salt comprises a tetrafluoroborate anion, a tetraalkylborate anion, a tetraarylborate anion, or a mixed fluoro/alkyl/aryl-borate anion.

9. The method of claim 1, wherein the biscationic palladium salt comprises a tetrafluoroborate anion.

10. The method of claim 1, wherein the biscationic palladium salt is generated in situ by the reaction of a palladium carboxylate complex with $HBF_4$.

11. The method of claim 1, wherein the biscationic palladium salt is $Pd(MeCN)_4(BF_4)_2$.

12. The method of claim 1, wherein the oxidizing agent is an optionally substituted quinone.

13. The method of claim 12, wherein the optionally substituted quinone comprises an optionally substituted anthroquinone, an optionally substituted benzoquinone, an optionally substituted naphthoquinone, an optionally substituted quinoline-5,8-dione, or an optionally substituted isoquinoline-5,8-dione.

14. The method of any one of claim 1, wherein the oxidizing agent is an optionally substituted quinone is present at a stoichiometric molar ratio of quinone to internal olefin in a range of from about 0.01 to about 1.1.

15. The method of claim 14, wherein the optionally substituted quinone is present at a stoichiometric molar ratio of quinone to internal olefin in a range of from about 0.9 to about 1.1.

16. The method of claim 1, wherein the oxidizing agent is a transition metal salt and the reaction mixture is in contacted with oxygen having a partial pressure in a range of from about 0.2 to about 2 atmospheres.

17. The method of claim 1, wherein the biscationic palladium salt is sufficiently active such at least 50 mol % of the internal olefin is converted into the ketone at a temperature in a range of about 10° C. to about 60° C. within 16 to 24 hrs.

18. The method of claim 1, wherein at least 75% of said ketone is formed on a carbon of the internal olefin.

19. The method of claim 1, wherein the internal olefin of the organic substrate is allylically functionalized, said functionalization comprising at least one functional group comprising a heteroatom on a carbon allylic to the internal olefin.

20. The method of claim 19, wherein the heteroatom comprises halo, N, S, or O.

21. The method of claim 19, wherein the functional group comprising a heteroatom comprises a —$CF(C_{1-6}$ alkyl$)_2$, —$CF_2(C_{1-6}$ alkyl), —$CF_3$, —N—, —S—, —O—, carbonyl, or thiocarbonyl moiety.

22. The method of claim 19, wherein the allylic carbon defines the internal olefin as having proximal and distal olefin carbons, said proximal olefin carbon being positioned closer to the allylic carbon than the distal olefin carbon, wherein the ratio of the ketone formed on the distal carbon relative to the ketone formed on the proximal carbon is at least about 10:1.

23. The method of claim 19, the solvent system containing essentially no secondary amide.

24. The method of claim 1, wherein the internal olefin of the organic substrate is allylically or homoallylically non-functionalized, such that the non-functionalized internal olefin is defined by the absence of an allylic or homoallylic substituent comprising a functional group having a heteroatom.

25. The method of claim 24, the solvent system comprising the at least one secondary alkyl amide.

26. The method of claim 1, wherein:
(i) the organic substrate has an initial allylically or homoallylically functionalized internal olefin, said functionalization comprising at least one functional group comprising a heteroatom on a carbon allylic or homoallylic to the internal olefin, respectively, said functional group comprising a halogen, —$CF(C_{1-6}$ alkyl$)_2$, —$CF_2(C_{1-6}$ alkyl), —$CF_3$, —N—, —S—, —O—, carbonyl, or thiocarbonyl moiety;
(ii) the solvent system consists essentially of acetonitrile and water, wherein the water is present at a level of 25 vol % or less, relative to the entire volume of the solvent system;
(iii) the biscationic palladium salt is generated in situ by the reaction of a palladium acetate complex with $HBF_4$, and is sufficiently active such at least 50 mol % of the internal olefin is converted into the ketone at a temperature in a range of about 10° C. to about 60° C. within 16 to 24 hrs; and
(iv) the oxidizing agent is benzoquinone, present at a stoichiometric molar ratio of benzoquinone to internal olefin in a range of from about 0.1 to about 2.5.

27. The method of claim 26, wherein the allylic carbon defines the internal olefin as having proximal and distal olefin carbons, said proximal olefin carbon being positioned closer to the allylic carbon than the distal olefin carbon, wherein the ratio of the ketone formed on the distal carbon relative to the ketone formed on the proximal carbon is at least about 10:1.

28. The method of claim 1, wherein:
(i) the organic substrate has an initial allylically or homoallylically non-functionalized internal olefin, such that the carbon allylic or homoallylic to the internal olefin, respectively, comprises only C—H, C—C, or both C—H and C—C bonds
(ii) the solvent system consists essentially of acetonitrile, N,N-dimethyl acetamide, and water; wherein the volume ratio of the acetonitrile to the N,N-dimethyl acetamide amide solvents is in a range of from about 0.8:1 to about 1:0.8 and the water is present at a level of 25 vol % or less, relative to the entire volume of the solvent system;
(iv) the biscationic palladium salt is generated in situ by the reaction of a palladium acetate complex with $HBF_4$, and is sufficiently active such at least 50 mol % of the internal olefin is converted into the ketone at a temperature in a range of about 10° C. to about 60° C. within 16 to 24 hrs; and
(v) the oxidizing agent is either (A) benzoquinone, present at a stoichiometric molar ratio of benzoquinone to internal olefin in a range of from about 0.1 to about 2.5; or (B) oxygen having a partial pressure in a range of from about 0.2 to about 2 atmospheres; or (C) both A and B.

29. The method of claim 26, wherein the biscationic palladium salt is $Pd(MeCN)_4(BF_4)_2$, generated in situ by the reaction of $Pd(OAc)_2$ with $HBF_4$.

30. The method of claim 28, wherein the biscationic palladium salt is $Pd(MeCN)_4(BF_4)_2$, generated in situ by the reaction of $Pd(OAc)_2$ with $HBF_4$.

31. The method of claim 6, wherein the water is present at a level of 25 vol % or less, relative to the entire volume of the solvent system.

32. The method of claim 20, wherein the heteroatom comprises fluoro, N, S, or O.

33. The method of claim 22, wherein the ratio of the ketone formed on the distal carbon relative to the ketone formed on the proximal carbon is at least about 20:1.

34. The method of claim 27, wherein the allylic carbon defines the internal olefin as having proximal and distal olefin carbons, said proximal olefin carbon being positioned closer to the allylic carbon than the distal olefin carbon, wherein the ratio of the ketone formed on the distal carbon relative to the ketone formed on the proximal carbon is at least about 20:1.

* * * * *